US008133684B2

(12) United States Patent
Aebersold et al.

(10) Patent No.: US 8,133,684 B2
(45) Date of Patent: Mar. 13, 2012

(54) METHODS TO DETERMINE ANDROGEN RESPONSES IN PROSTATE CELLS

(75) Inventors: Rudolf H. Aebersold, Mercer Island, WA (US); Michael E. Wright, Seattle, WA (US)

(73) Assignee: The Institute for Systems Biology, Seattle, WA (US)

( * ) Notice: Subject to any disclaimer, the term of this patent is extended or adjusted under 35 U.S.C. 154(b) by 147 days.

(21) Appl. No.: 12/372,644

(22) Filed: Feb. 17, 2009

(65) Prior Publication Data

US 2010/0196883 A1 Aug. 5, 2010

Related U.S. Application Data

(62) Division of application No. 10/325,442, filed on Dec. 20, 2002, now abandoned.

(51) Int. Cl.
G01N 33/53 (2006.01)
G01N 33/574 (2006.01)
(52) U.S. Cl. ........................................ 435/7.1; 435/7.23
(58) Field of Classification Search ........................ None
See application file for complete search history.

(56) References Cited

U.S. PATENT DOCUMENTS

| 5,840,708 | A | 11/1998 | Weiss |
| 5,968,737 | A | 10/1999 | Ali-Osman et al. |
| 5,994,076 | A | 11/1999 | Chenchik et al. |
| 5,995,309 | A | 11/1999 | Suzuki et al. |
| 6,335,170 | B1 | 1/2002 | Orntoft |
| 6,500,938 | B1 | 12/2002 | Au-Young et al. |
| 7,736,853 | B2 * | 6/2010 | Afar et al. ............... 435/6 |
| 2002/0166133 | A1 | 11/2002 | Barnes et al. |
| 2004/0170634 | A1 | 9/2004 | Burns et al. |

FOREIGN PATENT DOCUMENTS

WO WO 02/061087 A2 8/2002

OTHER PUBLICATIONS

Reubi et al (Cancer Research, 2000, 60:3105-3112).*
Solano et al (Cell Signal, 1999, 11:813-819).*
Internationally hyperlinked over proteins, "iHOP" "VIPR1", printed Jun. 19, 2011.*
Beato M., "Gene regulation by steroid hormones," *Cell* 56:335-344 (1989).
Bodey et al., "Failure of cancer vaccines: the significant limitations of this approach to immunotherapy," *Anticancer Res.* 20:2665-2676 (2000).
Boon T., "Toward a genetic analysis of tumor rejection antigens," *Adv. Cancer Res.* 58:177-210 (1992).
Bowie et al., Deciphering the message in protein sequences: tolerance to amino acid substitutions, *Science* 247:1306-1310 (1990).
Branch A.D., "A good antisense molecule is hard to find," *Trends Biochem. Sci.* 23:45-50 (1998).
Burgess et al., "Possible dissociation of the heparin-binding and mitogenic activities of heparin-binding (acidic fibroblast) growth factor-1 from its receptor-binding activities by site-directed mutagenesis of a single lysine residue," *J. Cell. Biol.* 111:2129-2138 (1990).
Curti B.D., Physical barriers to drug delivery in tumors, *Crit. Rev. Oncol. Hematol.* 14:29-39 (1993).
Deonarain M.P., "Ligand-targeted receptor-mediated vectors for gene delivery," *Expert Opin. Ther. Pat.* 8:53-69 (1998).
Evans R., "The steroid and thyroid hormone receptor superfamily", *Science* 240:889-895 (1998).
Gura T., "Systems for identifying new drugs are often faulty," *Science* 278:1041-1042 (1997).
Isaacs et al., "Androgen regulation of programmed death of normal and malignant prostatic cells", *J. Androl.* 13:457-464 (1992).
Isaacs J., "Role of androgens in prostatic cancer," *Vitam. Horm.* 49:433-502 (1994).
Jain R.K., "Barriers to drug delivery in solid tumors," *Sci. Am.* 271:58-65 (1994).
Kaiser J., "Cancer. First pass at cancer genome reveals complex landscape," *Science* 313:1370 (2006).
Lazar et al., "Transforming growth factor a: mutation of aspartic acid 47 and leucine 48 results in different biological activities," *Mol. Cell. Biol.* 8:1247-1252 (1988).
Lindzey et al., "Molecular mechanisms of androgen action", *Vitam. Horm.* 49:383-432 (1994).
Saffran et al., "Target antigens for prostate cancer immunotherapy", *Cancer Metastasis Rev.* 18:437-449 (1999).
Toulmé et al., "Modulation of RNA function by oligonucleotides recognizing RNA structure," *Prog. Nucleic Acid Res. Mol. Biol.* 69:1-46 (2001).
Verma and Somia, "Gene therapy—promises, problems and prospects," *Nature* 389:239-242 (1997).
Worby et al., "Science's STKE electronic resource—signal transduction knowledge environment," vol. 95, p. PL 1 (Aug. 2001).
MPSRCH search report, 2006, us-10-325-442-1.rni, pp. 1-2.
MPSRCH search report, 2006, us-10 325-442-1.rnpbm, pp. 7-8.

* cited by examiner

*Primary Examiner* — Laura B. Goddard
(74) *Attorney, Agent, or Firm* — Morrison & Foerster LLP

(57) ABSTRACT

The invention provides a method for diagnosing or predicting susceptibility to a prostate neoplastic condition in an individual. The method involves (a) determining a level of RDC1 in a sample from the individual, and (b) comparing the level of RDC1 in the sample to a reference level of RDC1, wherein a level of RDC1 in the sample 2-fold or more higher than the reference level indicates the presence of, or susceptibility to, a prostate neoplastic condition in the individual.

7 Claims, 3 Drawing Sheets

SEQUENCE LISTING

```
<160> NUMBER OF SEQ ID NOS: 3

<210> SEQ ID NO 1
<211> LENGTH: 1086
<212> TYPE: DNA
<213> ORGANISM: Homo sapiens

<400> SEQUENCE: 1
atggatctgc acctcttcga ctacgccgag ccaggcaact tctcggacat cagctggcca      60
tgcaacagca gcgactgcat cgtggtggac acggtgatgt gtcccaacat gcccaacaaa     120
agcgtcctgc tctacacgct ctccttcatt tacatttca tcttcgtcat cggcatgatt      180
gccaactccg tggtggtctg ggtgaatatc caggccaaga ccacaggcta tgacacgcac     240
tgctacatct tgaacctggc cattgccgac ctgtgggttg tcctcaccat cccagtctgg     300
gtggtcagtc tcgtgcagca caaccagtgg cccatgggcg agctcacgtg caaagtcaca     360
cacctcatct tctccatcaa cctcttcagc ggcattttct tcctcacgtg catgagcgtg     420
gaccgctacc tctccatcac ctacttcacc aacaccccca gcagcaggaa gaagatggta     480
cgccgtgtcg tctgcatcct ggtgtggctg ctggccttct gcgtgtctct gcctgacacc     540
tactacctga agaccgtcac gtctgcgtcc aacaatgaga cctactgccg gtccttctac     600
cccgagcaca gcatcaagga gtggctgatc ggcatggagc tggtctccgt tgtcttgggc     660
tttgccgttc ccttctccat tatcgctgtc ttctacttcc tgctggccag agccatctcg     720
gcgtccagtg accaggagaa gcacagcagc cggaagatca tcttctccta cgtggtggtc     780
ttccttgtct gctggctgcc ctaccacgtg gcggtgctgc tggacatctt ctccatcctg     840
cactacatcc ctttcacctg ccggctggag cacgccctct tcacggccct gcatgtcaca     900
cagtgcctgt cgctggtgca ctgctgcgtc aaccctgtcc tctacagctt catcaatcgc     960
aactacaggt acgagctgat gaaggccttc atcttcaagt actcggccaa aacagggctc    1020
accaagctca tcgatgcctc cagagtgtcg gagacggagt actccgcctt ggagcaaaac    1080
gccaag                                                             1086

<210> SEQ ID NO 2
<211> LENGTH: 362
<212> TYPE: PRT
<213> ORGANISM: Homo sapiens

<400> SEQUENCE: 2

Met Asp Leu His Leu Phe Asp Tyr Ala Glu Pro Gly Asn Phe Ser Asp
 1               5                   10                  15
```

Ile Ser Trp Pro Cys Asn Ser Ser Asp Cys Ile Val Val Asp Thr Val
            20                  25                  30

Met Cys Pro Asn Met Pro Asn Lys Ser Val Leu Leu Tyr Thr Leu Ser
                35                  40                  45

Phe Ile Tyr Ile Phe Ile Phe Val Ile Gly Met Ile Ala Asn Ser Val
        50                  55                  60

Val Val Trp Val Asn Ile Gln Ala Lys Thr Thr Gly Tyr Asp Thr His
 65                  70                  75                  80

Cys Tyr Ile Leu Asn Leu Ala Ile Ala Asp Leu Trp Val Val Leu Thr
                85                  90                  95

Ile Pro Val Trp Val Val Ser Leu Val Gln His Asn Gln Trp Pro Met
            100                 105                 110

Gly Glu Leu Thr Cys Lys Val Thr His Leu Ile Phe Ser Ile Asn Leu
            115                 120                 125

Phe Ser Gly Ile Phe Phe Leu Thr Cys Met Ser Val Asp Arg Tyr Leu
        130                 135                 140

Ser Ile Thr Tyr Phe Thr Asn Thr Pro Ser Ser Arg Lys Lys Met Val
145                 150                 155                 160

Arg Arg Val Val Cys Ile Leu Val Trp Leu Leu Ala Phe Cys Val Ser
                165                 170                 175

Leu Pro Asp Thr Tyr Tyr Leu Lys Thr Val Thr Ser Ala Ser Asn Asn
            180                 185                 190

Glu Thr Tyr Cys Arg Ser Phe Tyr Pro Glu His Ser Ile Lys Glu Trp
            195                 200                 205

Leu Ile Gly Met Glu Leu Val Ser Val Val Leu Gly Phe Ala Val Pro
        210                 215                 220

Phe Ser Ile Ile Ala Val Phe Tyr Phe Leu Leu Ala Arg Ala Ile Ser
225                 230                 235                 240

Ala Ser Ser Asp Gln Glu Lys His Ser Ser Arg Lys Ile Ile Phe Ser
                245                 250                 255

Tyr Val Val Val Phe Leu Val Cys Trp Leu Pro Tyr His Val Ala Val
            260                 265                 270

Leu Leu Asp Ile Phe Ser Ile Leu His Tyr Ile Pro Phe Thr Cys Arg
            275                 280                 285

Leu Glu His Ala Leu Phe Thr Ala Leu His Val Thr Gln Cys Leu Ser
        290                 295                 300

Leu Val His Cys Cys Val Asn Pro Val Leu Tyr Ser Phe Ile Asn Arg
305                 310                 315                 320

Asn Tyr Arg Tyr Glu Leu Met Lys Ala Phe Ile Phe Lys Tyr Ser Ala
                325                 330                 335

Lys Thr Gly Leu Thr Lys Leu Ile Asp Ala Ser Arg Val Ser Glu Thr
            340                 345                 350

Glu Tyr Ser Ala Leu Glu Gln Asn Ala Lys
        355                 360

<210> SEQ ID NO 3
<211> LENGTH: 15
<212> TYPE: PRT
<213> ORGANISM: Homo sapiens

<400> SEQUENCE: 3

Lys Thr Val Thr Ser Ala Ala Asn Asn Glu Thr Tyr Cys Arg Ser
 1               5                  10                  15

METHODS TO DETERMINE ANDROGEN RESPONSES IN PROSTATE CELLS

CROSS-REFERENCE TO RELATED APPLICATIONS

This application is a divisional of U.S. application Ser. No. 10/325,442, filed Dec. 20, 2002, and now abandoned, the entire contents of which is incorporated herein.

STATEMENT OF RIGHTS TO INVENTIONS MADE UNDER FEDERALLY SPONSORED RESEARCH

This invention was made with government support under grant number R33CA84698 awarded by the National Institutes of Health. The United States Government has certain rights in this invention.

BACKGROUND OF THE INVENTION

This invention relates generally to diagnosing neoplastic disease and, more specifically, to biomarkers that can be used to diagnose or determine a prognosis for prostate neoplastic disease, such as androgen-independent prostate cancer.

Cancer remains a major public health problem that profoundly affects the more than 1 million people diagnosed each year, as well as their families and friends. As our Nation's population grows and ages, more people will be diagnosed with cancer. Fortunately, the use of screening tests to detect cancers early often leads to more effective treatment with fewer side effects. Also, patients whose cancers are found early are less likely to die from their cancers than are those whose cancers are not found until symptoms appear.

Prostate cancer, which accounts for about 40 percent of all male cancers, is currently the most common type of cancer in American men and the second leading cause of cancer-related death in this population. An estimated 180,000 new cases of prostate cancer are diagnosed each year in the United States, and approximately 40,000 American men die of the disease annually.

Early stage prostate cancer is typically androgen-dependent, which means that the tumor cells require the hormone androgen to grow. A common strategy for treating this type of prostate cancer is androgen ablation therapy. The purpose of this therapy is to remove or reduce (ablate) the amount of androgen circulating in the individual to deprive cancer cells of this growth stimulating factor. When androgen ablation therapy is combined with traditional treatments, such as surgery or radiation therapy, most androgen-dependent prostate cancers are curable. However, some patients experience a relapse in prostate cancer that is refractory to the above treatment. These cancers are classified as androgen-independent and frequently become metastatic.

It is estimated that about 50% of all tumors considered to be localized in the prostate have already become metastatic and have escaped outside of the prostate. In many cases, such metastasized tumor cells, which are typically androgen-independent, are present in the patient at the time of diagnosis but are clinically undetectable. Difficulties in both detecting and treating late stage prostate cancers, such as androgen-independent prostate cancer, highlight the need for early detection.

Current methods for diagnosing prostate cancer are neither highly sensitive nor highly specific. Physical examination can miss small or centrally located tumors; serum prostate-specific antigen (PSA) determination detects both malignant and benign prostate disease; and sampling error in tissue biopsy may lead to erroneous benign diagnosis. At this time, other than PSA, few biomarkers specific for prostate cancer are in use, and no biomarkers specific for androgen-independent prostate cancer have been identified. This lack of biomarkers is unfortunate because improved early detection of prostate cancer can reduce mortality by improving chances for treating the cancer before it has spread.

Thus, there exists a need for identification of genes that can be used as diagnostic biomarkers and therapeutic targets for prostate cancer, such as androgen-independent prostate cancer. The present invention satisfies this need and provides related advantages as well.

SUMMARY OF THE INVENTION

The invention provides a method for diagnosing or predicting susceptibility to a prostate neoplastic condition in an individual. The method involves (a) determining a level of RDC1 in a sample from the individual, and (b) comparing the level of RDC1 in the sample to a reference level of RDC1, wherein a level of RDC1 in the sample 2-fold or more higher than the reference level indicates the presence of, or susceptibility to, a prostate neoplastic condition in the individual.

The invention provides another method for diagnosing or predicting susceptibility to a prostate neoplastic condition in an individual. The method involves (a) determining a level of a biomarker selected from a nucleic acid molecule having a GenBank accession number of: M18157, U75329, AF099989, AC005278, I38346, AF029684, M38690, AK000542, L06070, M27274, D29011, U35146, U72761, D87953, J03796, T34532, Y14436, AH011158, AL136939, U71321, AF154108, AB037745, U07643, D89053, AK022527, L36463, U28936, D43682, L04270, AF124141, AK025588, BC002374, U26644, AJ245222, AK026904, BC016318, X12433, U94777, L29008, AJ239387, U22526, AB020706, AB007153, AC011001, U19822, AF153330, S71949, U82761, AB040955, U78107, U18197, M65212, U85992, AB015019, D87464, T17320, AB034951, BC000749, AF170084, A49674, AB022017, JC6523, AB018298, AF015926, U83668, M17987, D42123, T00261, J03544, AB029020, U48734, AF061258, M77836, M28214, AB015317, M19383, JC4775, U44131, AB007851, M63180, U53347, AF112219, BC010037, A59253, D83004, M33308, AF060225, AK022489, BC012265, BC014514, AF100757, AF217190, BC009477, M22300, D00943, U39412, M28211, U51478, AB033001, AB029025, AF112227, L05628A, F006083, JEO350, M83751, T13151, AK024639, A53016, U47105, AB023420, AB011173, M69066, BC000176, AF024636, M98474, BC004821, JC1365, X61970, D14662, AC004839, AF128527, AY081219, AF001628, M33146 U48722, AF029890, M59828, T46901, T46250, AF188611, D89729, AB018541, L07493, L47162, BC000361, AF047042, M14221, L06505, U16738, BC000502, U83410, U23803, U63630, J04031, U17032, L22009, AF161494, U33635, X70649, M11146, U96132, AL035413, AF111168, M68840, M22382, T42692, L06499, AF214737, M29536, D13988, AK024512, JW0079, J04027, AF047472, BC008751, I53799, X78136, AF057740, A57099, AC003972, M93107, AF157317, AF161507, BC002505, X78933, AB039669, U78027, AF041483, BC003092, M15661, AB032903, L13848, J03826, AB043007, J02966, A55575, L35946, AF111713, D16481, X61100, M28372, AF177344, T09073, AF154502, I55595, S63912, AK000501, M28880, M34424, AH003217, S78046, U24105, U64791, M55905, D49396, M32325, U28811, D16480, D38112, AB007867, A49656, AL035689, U23143, X71129, AB046803, S69272, L08666, BC002479, AL023805, U25064, AB004574, AF277719, M94314, B53737, U15008, AF242773, BC007321, U30894, AF007833, AK025822, BC009244, AF043250, X64044, D17532, AJ245620, J04444, AF044953, M30448, M22636, D21163, AF30405, BC002348, BC007904, AK022590, U60266, D16561, D26361, AC002540, A54601 J04810, AF053069, M60854, BC018340, AF018956, D50420, AF220049, AF150087, L04636, AL035079, AF146192, M80254, U17248, L16842, U96114, X92689 AF015812, M33374, D86061, D87073, AF047470, M63488, AF151817, AF026977, AK001714, BC022414, M96982, J04058, AF042284, M36647, L06132, AB018266, M94046, D14710, J03225, AF151809, L06498, J04973, M35410, D10511, BC001454, J03250, AAC41754, BC001795, X12671, AF068846, D30648, AF038962, AF161397, M57424, U34355, BC007295, U59321, AF085361, AF181120, AJ001258, AF017456, M96684, AC004528, D87686, S70314, AC004957, U74628, AF087135, AF047434, AC005609, AK024450, L41351, U25165, BC001015, AL023881, L12387, X83425 U29091, M15353, AB000449, X03444, D25328, L29555, M11354, BAA09768, AB006537, M34458, X73459, T08789, AF002668, U12424, L14599, AK022587, X62137, M55210, L22253, M64749, M22430, AF057145, AJ002744, AB014511, AJ278775, S12444, AB028980, and D26135, or an encoded polypeptide, in a sample from the individual, and (b) comparing the level of the biomarker in the sample to a reference level of the biomarker, wherein a level of the biomarker in the sample 2-fold or more higher than the reference level of the biomarker indicates the presence of, or susceptibility to, a prostate neoplastic condition in the individual.

In particular embodiments, a method of the invention can be used for diagnosing or predicting susceptibility to metastatic prostate cancer or androgen-independent prostate cancer. A method of the invention also can be used to determine if an individual tested is at risk for relapse of disease, to determine a proper course of treatment for an individual tested, and to determine a prognosis for survival for an individual tested.

The invention also provides a method for decreasing prostate cell growth in a mammal. The method involves administering to the mammal an amount of an RDC1 antagonist effective to decrease prostate cell growth in the mammal. In an embodiment, prostate cell growth decreased is androgen-independent growth.

The invention further provides a method for screening for a compound for decreasing prostate cell growth. The method involves (a) contacting a compound that is an RDC1 antagonist with a prostate cell; and (b) determining a proliferation state of the cell, wherein a compound that reduces proliferation of the cell is identified as a compound that decreases prostate cell growth.

Also provided by the invention is a method for targeting a therapeutic moiety for treatment of a prostate neoplastic condition. The method involves linking the therapeutic moiety to a RDC1 binding agent.

DETAILED DESCRIPTION OF THE INVENTION

Figure 1A:
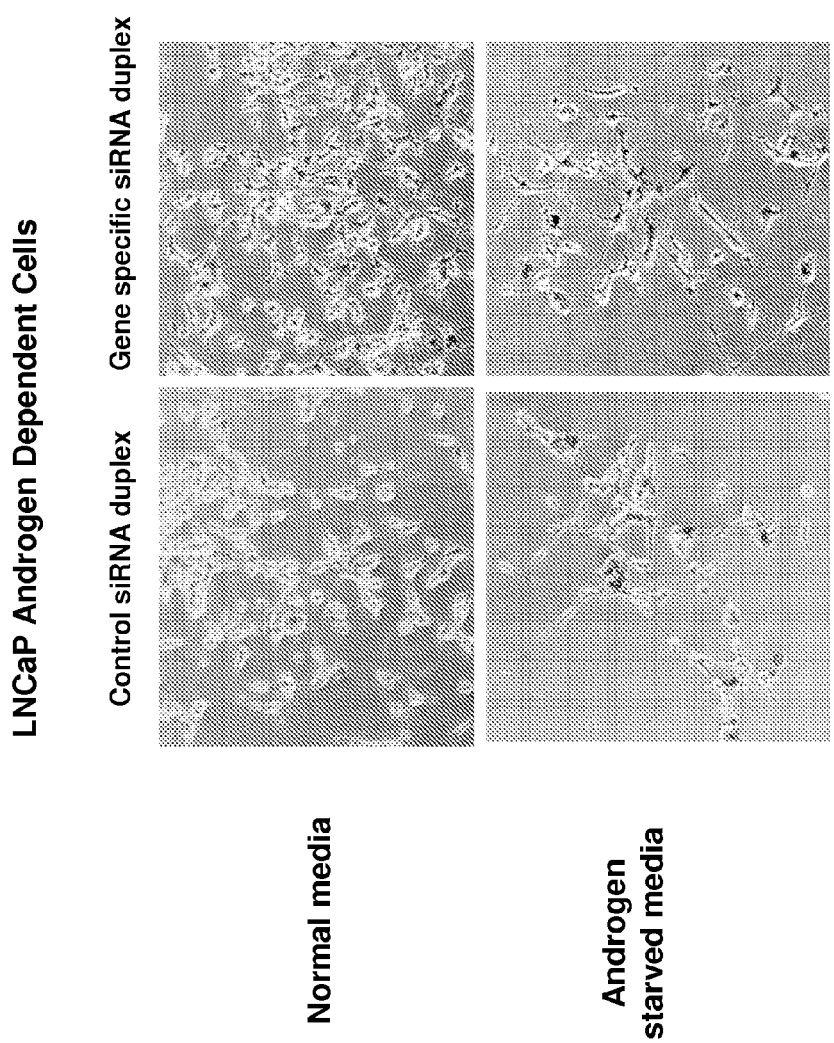
FIG. 1 shows that LNCaP cells (FIGS. 1A and 1C) and cells of an androgen independent cell line (FIG. 1B) contain an RDC1 gene-specific siRNA duplex have an altered adhesion phenotype as compared to control cells that contain a scrambled siRNA duplex.

This invention relates to the discovery that several polypeptides have altered expression levels in androgen-treated prostate cancer cells compared to non-treated prostate cells. The identified polypeptides and nucleotide sequences encoding them are useful as diagnostic biomarkers for neoplastic conditions of the prostate and as therapeutic targets.

As described in Example I, isotope-coded affinity tag (ICAT) technology was used to identify a plurality of polypeptides that undergo changes in expression levels in prostate cells in response to the hormone androgen. This analysis was focused on proteins that reside in the microsomal fraction of LNCaP prostate epithelial cells. In particular, a G-protein coupled receptor (GPCR) was identified to have reduced expression in androgen-treated prostate cells. This GPCR, which is an orphan GPCR known as RDC1, was further demonstrated to have a role in migration and cell attachment, and in sustaining survival of androgen-treated cells. As shown in Example I, a reduction in expression of RDC1 by RNA interference results in a phenotypic change characterized by increased cell adhesion, which is consistent with a less proliferative state. Additionally, about 1580 other proteins that have altered expression in androgen-treated prostate cells were identified using ICAT technology. Based on the identification of proteins having altered expression in response to androgen, the invention provides methods for diagnosing prostate neoplastic conditions, and in particular, androgen-independent prostate cancer.

In one embodiment, the invention is directed to a method for diagnosing or predicting susceptibility to a prostate neoplastic condition. A biomarker used in the methods of the invention, such as the androgen-regulated gene RDC1 or any of the biomarkers listed by GenBank accession number in Table 1, is expressed in prostate cells and becomes elevated or reduced in response to androgen. Such a biomarker can be used as a specific marker for prostate neoplastic conditions, and in particular, androgen-independent prostate cancer.

The diagnostic and predictive methods of the invention also are useful for determining if a patient is at risk for relapse. Despite undergoing complete surgical removal of the cancer, about 50% of patients with advanced prostate experience recurrence of their cancer. Many patients with advanced prostate cancer already have small amounts of cancer that have spread outside the prostate and were not removed by surgery. Some advanced prostate cancers become unresponsive to androgen ablation therapy, even when this therapy is combined with other modalities. Such cancers are referred to as androgen-independent prostate cancers, and they cannot be reliably detected with any of the currently available tests. The diagnostic and predictive methods of the invention can be used to identify surgically treated patients likely to experience cancer recurrence, for example, due to the presence of androgen-independent prostate cancer cells. Patients so identified can be offered additional therapeutic options, including preoperative or postoperative adjuncts such as chemotherapy, radiation, biological modifiers and other suitable therapies. The methods can be effective for determining the risk of relapse or metastasis in patients who demonstrate no measurable metastasis at the time of examination or surgery.

As used herein, the term "level" is intended to mean the amount, accumulation or rate of synthesis of a biomarker molecule. A level can be represented, for example, by the amount or synthesis rate of messenger RNA (mRNA) encoded by a gene, the amount or synthesis rate of polypeptide corresponding to a given amino acid sequence encoded by a gene, or the amount or synthesis rate of a biochemical form of a molecule accumulated in a cell, including, for example, the amount of particular post-synthetic modifications of the nucleic acid or polypeptide. The term can be used to refer to an absolute amount of a molecule in a sample or to a relative amount of the molecule, including amounts determined under steady-state or non-steady-state conditions. The level of a molecule can be determined relative to a control molecule in a sample. The level of a molecule also can be referred to as an expression level.

A nucleic acid level is intended to mean the amount, accumulation or rate of synthesis of an RNA encoded by a biomarker gene. The nucleic acid level can be represented by, for example, the amount or transcription rate of hnRNA or mRNA encoded by a gene. A nucleic acid level similarly refers to an absolute or relative amount or a synthesis rate determined, for example, under steady-state or non-steady-state conditions.

A polypeptide level is intended to mean the amount, accumulation or rate of synthesis of a biomarker polypeptide. The polypeptide expression level can be represented by, for example, the amount or rate of synthesis of the polypeptide, a precursor form or a post-translationally modified form of the polypeptide. Various biochemical forms of a polypeptide resulting from post-synthetic modifications can be present in a sample.

Such modifications include post-translational modifications, proteolysis, and formation of macromolecular complexes. Post-translational modifications of polypeptides include, for example, phosphorylation, lipidation, prenylation, sulfation, hydroxylation, acetylation, addition of carbohydrate, addition of prosthetic groups or cofactors, formation of disulfide bonds and the like. In addition, it is understood that fragments of a polypeptide are included within the definition of a polypeptide level. Fragments can include, for example, amino terminal, carboxyl terminal, or internal deletions of a full length polypeptide. Accumulation or synthesis rate with or without such modifications is included with in the meaning of the term. Similarly, a polypeptide level also refers to an absolute amount or a synthesis rate of the polypeptide determined, for example, under steady-state or non-steady-state conditions.

When used in reference to RDC1 mRNA or polypeptide, the term level refers to the extent, amount or rate of synthesis of the nucleic acid sequence referenced as SEQ ID NO:1 or the RDC1 polypeptide referenced as SEQ ID NO:2, or substantially the same nucleotide or amino acid sequence.

When used in reference to a biomarker selected from those listed in Table 1, the term refers to the extent, amount or rate of synthesis of the nucleic acid sequence referenced by nucleic acid accession number or the corresponding polypeptide referenced by protein accession number, or substantially the same nucleotide or amino acid sequence.

The level of a nucleic acid molecule or polypeptide having a nucleotide or amino acid sequence that is substantially the same as a reference sequence, such as a biomarker sequence used in a method of the invention, can be determined using a nucleotide probe or binding agent that is specifically reactive with the reference nucleotide or amino acid sequence.

A nucleotide sequence that is substantially the same as a reference nucleotide sequences contains a considerable degree of sequence identity or similarity, such as at least 70%, 80%, 90%, 95%, 98%, or 100% sequence identity to the reference nucleotide sequence. Differences can be naturally occurring genetic differences between individuals, such as mutations and polymorphisms of a gene, or can result from cloning or amplifying a reference nucleic acid molecule.

An amino acid sequence that has substantially the same amino acid sequence as a reference amino acid sequence contains a considerable degree of sequence identity or similarity, such as at least 70%, 80%, 90%, 95%, 98%, or 100% sequence identity to a reference amino acid sequence. Amino acid changes, gaps and insertions can be naturally occurring mutations, or can result from processing a sample containing the polypeptide.

Differences between nucleotide and amino acid sequences can be determined using available algorithms and programs such as the Smith-Waterman algorithm and the BLAST homology search program (Altschul et al., *J. Mol. Biol.* 215: 403-410 (1990)).

As used herein, the term "reference level" is intended to mean a control level of a biomarker nucleic acid, polypeptide, or fragment thereof, used to evaluate a test level of a biomarker nucleic acid, polypeptide, or fragment thereof, in a sample from an individual. A reference level can be a normal reference level or a disease-state reference level. A normal reference level is an amount of expression of a biomarker nucleic acid, polypeptide, or fragment thereof, in a non-neoplastic cell, such as a non-neoplastic prostate cell. A disease-state reference level is an amount of expression of a biomarker nucleic acid, polypeptide, or fragment thereof, in a neoplastic cell, such as a benign prostate tumor cell, malignant prostate tumor cell, androgen-dependent prostate tumor cell, androgen-independent prostate tumor cell or other abnormally proliferating prostate cell. A reference level also can be a stage-specific reference level. A stage-specific reference level refers to a level of a biomarker nucleic acid, polypeptide, or fragment thereof, expression characteristic of a given stage of progression of a prostate tumor. Stages of progression of prostate cancer are described herein below. The reference level can also be a level of a biomarker contained in in vitro cultured cells that can be manipulated to simulate tumor cells, or can be manipulated in any other manner that yields a level that accurately reflects a reference level for a particular biomarker.

As used herein, the term "nucleic acid" is intended to mean a single- or double-stranded DNA or RNA molecule including, for example, genomic DNA, cDNA and mRNA. The term is intended to include nucleic acid molecules of both synthetic and natural origin. A nucleic acid can be of linear, circular or branched configuration, and can represent either the sense or antisense strand, or both, of a native nucleic acid molecule.

As described herein, the term "prostate neoplastic condition" is intended to mean a malignant, or metastatic prostate lesion of proliferating cells. The term includes primary prostate tumors, which can be classified according to various nomenclatures. For example, a primary prostate tumor can be classified into stages TX, T0, T1, T2, T3, and T4. Metastatic prostate tumors can be classified into stages, such as stages D1, D2, and D3. In one embodiment, the term includes a malignant, or metastatic prostate lesion. In another embodiment the term excludes benign prostatic hypertrophy.

As used herein, the term "binding agent" when used in reference to a biomarker polypeptide, is intended to mean a compound, a macromolecule, including polypeptide, DNA, RNA and carbohydrate that selectively binds a biomarker polypeptide or fragment thereof. For example, a binding agent can be a polypeptide that selectively binds with high affinity or avidity to a biomarker polypeptide without substantial cross-reactivity with other polypeptides that are unrelated to the biomarker polypeptide. The affinity of a binding agent that selectively binds a biomarker polypeptide will generally be greater than about $10^{-5}$ M, such as greater than about $10^{-6}$ M, including greater than about $10^{-8}$ M and greater than about $10^{-9}$ M. Specific samples of such selective binding agents include a polyclonal or monoclonal antibody specific for a biomarker polypeptide or a peptide, nucleic acid, nucleic acid analog, or small organic molecule, identified, for example, by affinity screening of a library. For certain applications, a binding agent can be used that preferentially recognizes a particular conformational or post-translationally modified state of a biomarker polypeptide. The binding agent can be labeled with a detectable moiety, if desired, or rendered detectable by specific binding to a detectable secondary binding agent.

A detectable label can be a molecule that renders a binding agent or nucleic acid probe detectable by an analytical method. An appropriate detectable label depends on the particular assay format; detectable labels are well known by those skilled in the art. For example, a detectable label can be a measurable moiety such as a radioisotope, fluorochrome, chemiluminescent marker, biotin, or other moiety known in the art that is measurable by analytical methods. A detectable label also can be a nucleic acid molecule without a measurable moiety. For example, PCR or RT-PCR primers can be used without conjugation to selectively amplify all or a desired portion of a biomarker nucleic acid molecule. The amplified nucleic acids can then be detected by methods known in the art.

As used herein, the term "RDC1" is intended to mean a polypeptide having substantially the same amino acid sequence as SWISS-PROT entry P25106, referenced as SEQ ID NO:2, and encoded by substantially the same nucleotide sequence as GenBank entry M64749, referenced as SEQ ID NO:1. Briefly, RDC1 is a G-protein coupled receptor expressed in neoplastic prostate cells. As shown herein, expression of RDC1 is reduced in prostate cells upon exposure of the cells to an androgen, such as androsterone or testosterone. Androgens are steroid male sex hormones that bind to steroid receptor superfamily members and direct development of the male reproductive system and production and maintenance of secondary sexual characteristics. Non-limiting examples of androgens include testosterone and andosterone, and modified forms of these hormones, such as, for example, alkylated forms of testosterone, including methyl testosterone and fluoxymesterone, and esterified forms of testosterone.

As used herein, the term "cancer" is intended to mean a class of diseases characterized by the uncontrolled growth of aberrant cells, including all known cancers, and neoplastic conditions, whether characterized as malignant, benign, soft tissue or solid tumor. Specific cancers include prostate cancer, malignant prostate cancer, and androgen-independent prostate cancer.

The term "androgen-independent," when used in reference to a prostate cell or prostate tumor cell, is intended to mean that the cell is capable of proliferating in the absence of androgen.

As used herein, the term "prostate cell" is intended to mean a cell contained in, or obtained from, the prostate of an individual. A prostate cell can be contained within a tissue sample, can be an isolated cell and can be a cell placed in or adapted to tissue culture. A benign or metastatic tumor of the prostate can contain neoplastic cells. Therefore, a prostate cell can be a normal prostate cell or neoplastic prostate cell, including a malignant prostate cell.

As used herein, the term "neoplastic cell" is intended to mean any cell that is transformed such that it proliferates without normal homeostatic growth control. A neoplastic prostate cell can proliferate in response to androgen (androgen-dependent growth) or independently of androgen (androgen-independent growth). Generally, later stage prostate cancers, including metastatic prostate cancers, have a higher likelihood of being androgen-independent than earlier stage cancers, which are typically androgen-dependent. Therefore, a neoplastic cell contained in a sample tested in a method of the invention can be androgen-dependent or androgen-independent.

As used herein, the term "sample" is intended to mean any biological fluid, cell, tissue, organ or portion thereof, that includes or potentially includes a prostate cell, such as a neoplastic prostate cell. The term includes a sample present in an individual as well as a sample obtained or derived from the individual. As a non-limiting example, a sample can be a histologic section of a specimen obtained by biopsy, or a cell that is placed in or adapted to tissue culture. A sample further can be a subcellular fraction or extract, or a crude or substantially pure nucleic acid molecule or protein preparation.

As used herein, the term "risk for relapse" is intended to mean the probability of tumor recurrence or spread in an individual subsequent to diagnosis of cancer. Tumor recurrence refers to further growth of neoplastic or cancerous cells after diagnosis of cancer. Particularly, recurrence can occur when further cancerous cell growth occurs in the cancerous tissue. Tumor spread refers to dissemination of cancer cells into local or distant tissues and organs, for example during tumor metastasis. Tumor recurrence, in particular, metastasis, is a significant cause of mortality among patients who have undergone surgical treatment for prostate cancer.

RDC1 is a G-protein coupled receptor that is present at higher levels in androgen-treated prostate cells than in untreated prostate cells. RDC1 is the human ortholog of the canine RDC1 gene and was originally reported to be a vasoactive intestinal peptide (VIP) receptor (Sreedharan et al., *Proc. Natl. Acad. Sci. U.S.A.* 88:4986-4990 (1991)). However, several references suggest that this GPCR does not function as a VIP receptor (Nagata S. et al. *Trends Pharmacol. Sci.* 13:102-103 (1992)). RDC1 has more recently been reported to be an orphan chemokine receptor (Heesen et al. *Immunogenetics* 47(5):364-709 (1998)), and an adrenomedullin receptor (Autelitano et al. *Clin Sci.* (London), 96(5) 493-498 (1999); and U.S. Pat. No. 6,197,069). RDC1 has also been reported to be a co-receptor for human and simian immunodeficiency viruses (Shimizu et al. *J. Virology* 74:619-626 (2000)). As shown herein, RDC1 can be used as biomarker for diagnosing, predicting susceptibility to, and determining a prognosis for a prostate neoplastic condition.

The invention provides other biomarkers for diagnosing, predicting susceptibility to and determining a prognosis for a prostate neoplastic conditions. The biomarker protein and nucleic acid accession numbers shown in Table I correspond to proteins identified to have a change in expression of at least 1.6 fold in response to androgen, and nucleic acid molecules that encode these proteins. The proteins identified to undergo increased or reduced expression in response to androgen have a variety of cellular functions. For example, one has a role in aging; twenty-eight have a role in amino acid metabolism; one has a role in axonal transport; fifty-four have a role in carbohydrate metabolism; thirty-three have a role in cell adhesion; forty-one have a role in cell cycle control; five have a role in cell elongation; three have a role in cell polarity; twenty-nine have a role in cell stress; seventy-one have a role in cell structure; nine have a role in chromatin/chromosome structure; one has a role in cytokinesis; ten have a role in DNA repair; seven have a role in DNA synthesis; fifty-one have a role in differentiation; one has a role in dosage compensation; seventy-four have a role in energy generation; fifty have a role in lipid, rat and sterol metabolism; two have a role in meiosis; seventeen have a role in membrane fusion; thirteen have a role in mitosis; twenty-one have a role in nuclear-cytoplasmic transport; fifty-six have a role in nucleotide metabolism; thirty-three have a role in other metabolism; one has a role in phosphate metabolism; one has a role in Pol III transcription; thirty-eight have a role in Pol II transcription; fourteen have a role in protein complex assembly; fifty-two have a role in protein degradation; twenty-eight have a role in protein folding; sixty-seven have a role in protein modification; eighty-four have a role in protein synthesis; twenty-eight have a role in protein translocation; forty-eight have a role in RNA processing/modification; fourteen have a role in RNA splicing; nine have a role in RNA turnover; eight have a role in recombination; one hundred and forty-five have a role in signal transduction; sixty-one have a role in small molecule transport; sixty-eight have a role in vesicular transport; and four have a role in virulence. Regardless of cell function, any of these proteins or nucleic acid molecules that encode them can be used as a biomarker to diagnose, predict susceptibility to, or determine a prognosis for, a prostate neoplastic condition.

The invention provides a method of diagnosing or predicting prostate neoplastic conditions based on the finding of a positive correlation between expression of RDC1, in prostate cells and the ability of the cells to proliferate in the absence of androgen. The diagnostic methods of the invention are applicable to numerous prostate neoplastic conditions and pathologies as described above. One characteristic of prostate tumor cells that have progressed into a state of androgen-independent growth can be increased expression of RDC1 and other biomarkers identified by GenBank accession number in Table 1. Androgen-independent growth can be a characteristic of metastatic prostate cells and prostate tumor cells that are refractory to androgen-ablation therapy. An increase in RDC1 expression, or an increase in expression of a biomarker shown in Table 1, in an individual having a prostate neoplastic condition can be determined by comparing the amount of RDC1 or other biomarker to that found, for example, in a normal prostate tissue sample. A two-fold or more increase in RDC1 or other biomarker expression in a sample from an individual relative to a sample obtained from normal prostate cells or from an androgen-dependent cell line can be indicative of a prostate neoplastic condition.

As a diagnostic indicator, RDC1 or another biomarker shown in Table 1, can be used qualitatively to positively identify a prostate neoplastic condition, such as an androgen-independent prostate neoplastic condition, as described above. Alternatively, RDC1 or another biomarker shown in Table 1, can be used quantitatively to determine the degree of susceptibility to, or a prognosis for, a prostate neoplastic condition. For example, successive increases in the level of RDC1, or other biomarker shown in Table 1, can be used as a predictive indicator of the degree or severity of a prostate neoplastic condition because increased expression, leading to a rise in accumulated levels can positively correlate with increased androgen-independent growth of prostate tumor cells. A higher level of RDC1, or another biomarker shown in Table 1, can be correlated with a later the stage of a prostate neoplastic condition because metastatic prostate cells are typically characterized by androgen-independent growth.

One or more biomarkers referenced in Table 1 can be used together in a method of the invention. In addition, two or more, three or more, four or more, five or more, or six or more biomarkers referenced in Table 1 can be used together in a method of the invention.

Correlative increases can be determined by comparison of level of a biomarker from an individual having, or suspected of having a neoplastic condition of the prostate to a level of the biomarker from known samples determined to exhibit a prostate neoplastic condition. Alternatively, correlative increases can be determined by comparison of a level of a biomarker from the test individual to levels of other known markers of prostate cancer such as prostate specific antigen (PSA), glandular kallikrein 2 (hK2) and prostase/PRSS18. These other known markers can be used, for example, as an internal or external standard for correlation of stage-specific expression with increases in RDC1 level and severity of the neoplastic or pathological condition. Conversely, a regression in the severity of a prostate neoplastic condition is followed by a corresponding decrease in a level of a biomarker and can similarly be assessed using the methods described above.

Given the teachings and guidance provided herein, those skilled in the art will know or can determine the stage or severity of a prostate neoplastic condition based on a determination of expression of a biomarker and using known procedures and marker comparisons other than those described above. For a review of recognized values for such other marker in normal versus pathological tissues, see for example, *Campbell's Urology*, Seventh Edition, W.B. Saunders Company, Philadelphia (1998).

Therefore, the invention provides a method for diagnosing or predicting susceptibility to a prostate neoplastic condition in an individual. The method involves (a) determining a level of RDC1 in a sample from the individual, and (b) comparing the level of RDC1 in the sample to a reference level of RDC1, wherein a level of RDC1 in the sample 2-fold or more higher than the reference level of RDC1 indicates the presence of, or susceptibility to, a prostate neoplastic condition in the individual.

The invention provides another method for diagnosing or predicting susceptibility to a prostate neoplastic condition in an individual. The method involves (a) determining a level of a biomarker selected from a nucleic acid molecule having a GenBank accession number of: M18157, U75329, AF099989, AC005278, I38346, AF029684, M38690, AK000542, L06070, M27274, D29011, U35146, U72761, D87953, J03796, T34532, Y14436, AH011158, AL136939, U71321, AF154108, AB037745, U07643, D89053, AK022527, L36463, U28936, D43682, L04270, AF124141, AK025588, BC002374, U26644, AJ245222, AK026904, BC016318, X12433, U94777, L29008, AJ239387, U22526, AB020706, AB007153, AC011001, U19822, AF153330, S71949, U82761, AB040955, U78107 U18197, M65212, U85992, AB015019, D87464, T17320, AB034951, BC000749, AF170084, A49674, AB022017, JC6523, AB018298, AF015926, U83668, M17987, D42123, T00261, J03544, AB029020, U48734, AF061258, M77836, M28214, AB015317, M19383, JC4775, U44131, AB007851, M63180, U53347, AF112219, BC010037, A59253, D83004, M33308, AF060225, AK022489, BC012265, BC014514, AF100757, AF217190, BC009477, M22300, D00943, U39412, M28211, U51478, AB033001, AB029025, AF112227, L05628A, F006083, JEO350, M83751, T13151, AK024639, A53016, U47105, AB023420, AB011173, M69066, BC000176, AF024636, M98474, BC004821, JC1365, X61970, D14662, AC004839, AF128527, AY081219, AF001628, M33146 U48722, AF029890, M59828, T46901, T46250, AF188611, D89729, AB018541, L07493, L47162, BC000361, AF047042, M14221, L06505, U16738, BC000502, U83410, U23803, U63630, J04031, U17032, L22009, AF161494, U33635, X70649, M11146, U96132, AL035413, AF111168, M68840, M22382, T42692, L06499, AF214737, M29536, D13988, AK024512, JW0079, J04027, AF047472, BC008751, I53799, X78136, AF057740, A57099, AC003972, M93107, AF157317, AF161507, BC002505, X78933, AB039669, U78027, AF041483, BC003092, M15661, AB032903, L13848, J03826, AB043007, J02966, A55575, L35946, AF111713, D16481, X61100, M28372, AF177344, T09073, AF154502, I55595, S63912, AK000501, M28880, M34424, AH003217, S78046, U24105, U64791, M55905, D49396, M32325, U28811, D16480, D38112, AB007867, A49656, AL035689, U23143, X71129, AB046803, S69272, L08666, BC002479, AL023805, U25064, AB004574, AF277719, M94314, B53737, U15008, AF242773, BC007321, U30894, AF007833, AK025822, BC009244, AF043250, X64044, D17532, AJ245620, J04444, AF044953, M30448, M22636, D21163, AF30405, BC002348, BC007904, AK022590, U60266, D16561, D26361, AC002540, A54601 J04810, AF053069, M60854, BC018340, AF018956, D50420, AF220049, AF150087, L04636, AL035079, AF146192, M80254, U17248, L16842, U96114, X92689 AF015812, M33374, D86061, D87073, AF047470, M63488, AF151817, AF026977, AK001714, BC022414, M96982, J04058, AF042284, M36647, L06132, AB018266, M94046, D14710, J03225, AF151809, L06498, J04973, M35410, D10511, BC001454, J03250, AAC41754, BC001795, X12671, AF068846, D30648, AF038962, AF161397, M57424, U34355, BC007295, U59321, AF085361, AF181120, AJ001258, AF017456, M96684, AC004528, D87686, S70314, AC004957, U74628, AF087135, AF047434, AC005609, AK024450, L41351, U25165, BC001015, AL023881, L12387, X83425 U29091, M15353, AB000449, X03444, D25328, L29555, M11354, BAA09768, AB006537, M34458, X73459, T08789, AF002668, U12424, L14599, AK022587, X62137, M55210, L22253, M64749, M22430, AF057145, AJ002744, AB014511, AJ278775, S12444, AB028980, and D26135, or an encoded polypeptide, in a sample from the individual, and (b) comparing the level of the biomarker in the sample to a reference level of the biomarker, wherein a level of the biomarker in the sample 2-fold or more higher than the reference level of the biomarker indicates the presence of, or susceptibility to, a prostate neoplastic condition in the individual.

In particular embodiments, the biomarker can be selected from a nucleic acid molecule having a GenBank accession number of M18157, U75329, AF099989, AC005278, I38346, AF029684, M38690, AK000542, L06070, M27274, D29011, U35146, U72761, D87953, J03796, T34532, Y14436, AH011158, AL136939, U71321, AF154108, AB037745, U07643, D89053, AK022527, L36463, U28936, D43682, L04270, AF124141, AK025588, BC002374, U26644, AJ245222, AK026904, BC016318, X12433, U94777, L29008, AJ239387, U22526, AB020706, AB007153, AC011001, U19822, AF153330, S71949, U82761, AB040955, U78107, or an encoded polypeptide; from a nucleic acid molecule having a GenBank accession number of U18197, M65212, U85992, AB015019, D87464, T17320, AB034951, BC000749, AF170084, A49674, AB022017, JC6523, AB018298, AF015926, U83668, M17987, D42123, T00261, J03544, AB029020, U48734, AF061258, M77836, M28214, AB015317, M19383, JC4775, U44131, AB007851, M63180, U53347, AF112219, BC010037, A59253, D83004, M33308, AF060225, AK022489, BC012265, BC014514, AF100757, AF217190, BC009477, M22300, or an encoded polypeptide; from a nucleic acid molecule having a GenBank accession number of D00943, U39412, M28211, U51478, AB033001, AB029025, AF112227, L05628A, F006083, JEO350, M83751, T13151, AK024639, A53016, U47105, AB023420, AB011173, M69066, BC000176, AF024636, M98474, BC004821, JC1365, X61970, D14662, AC004839, AF128527, AY081219, AF001628, M33146, or an encoded polypeptide; from a nucleic acid molecule having a GenBank accession number of U48722, AF029890, M59828, T46901, T46250, AF188611, D89729, AB018541, L07493, L47162, BC000361, AF047042, M14221, L06505, U16738, BC000502, U83410, U23803, U63630, J04031, U17032, L22009, AF161494, U33635, X70649, M11146, or an encoded polypeptide; from a nucleic acid molecule having a GenBank accession number of U96132, AL035413, AF111168, M68840, M22382, T42692, L06499, AF214737, M29536, D13988, AK024512, JW0079, J04027, AF047472, BC008751, I53799, X78136, AF057740, A57099, AC003972, M93107, AF157317, AF161507, BC002505, X78933, AB039669, U78027, AF041483, BC003092, M15661, AB032903, L13848, J03826, AB043007, J02966, or from an encoded polypeptide; from a nucleic acid molecule having a GenBank accession number of A55575, L35946, AF111713, D16481, X61100, M28372, AF177344, T09073, AF154502, I55595, S63912, AK000501, M28880, M34424, AH003217, S78046, U24105, U64791, M55905, D49396, M32325, U28811, D16480, D38112, AB007867, A49656, AL035689, U23143, X71129, AB046803, S69272, L08666, BC002479, AL023805, U25064, AB004574, AF277719, M94314, B53737, U15008, AF242773, BC007321, U30894, AF007833, AK025822, BC009244, AF043250, X64044, D17532, AJ245620, J04444, AF044953, M30448, M22636, D21163, AF30405, BC002348, or an encoded polypeptide; from a nucleic acid molecule having a GenBank accession number of BC007904, AK022590, U60266, D16561, D26361, AC002540, A54601 J04810, AF053069, M60854, BC018340, AF018956, D50420, AF220049, AF150087, L04636, AL035079, AF146192, M80254, U17248, L16842, U96114, X92689 AF015812, M33374, D86061, D87073, AF047470, M63488, AF151817, AF026977, AK001714, BC022414, M96982, J04058, AF042284, M36647, L06132, AB018266, M94046, D14710, J03225, AF151809, L06498, J04973, M35410, D10511, BC001454, J03250, AAC41754, BC001795, X12671, AF068846, D30648, AF038962, AF161397, M57424, U34355, BC007295, U59321, AF085361, AF181120, AJ001258, AF017456, M96684, or an encoded polypeptide; from a nucleic acid molecule having a GenBank accession number of AC004528, D87686, S70314, AC004957, U74628, AF087135, AF047434, AC005609, AK024450, L41351, U25165, BC001015, AL023881, L12387, X83425 U29091, M15353, AB000449, X03444, D25328, L29555, M11354, BAA09768, AB006537, M34458, X73459, T08789, AF002668, U12424, L14599, AK022587, X62137, M55210, L22253, M64749, M22430, AF057145, AJ002744, AB014511, AJ278775, S12444, AB028980, and D26135, or an encoded polypeptide.

A prostate neoplastic condition is characterized by a benign or malignant prostate lesion of proliferating cells. Prostate neoplastic conditions include, for example, prostate interepithelial neoplasia (PIN) and prostate cancer. Prostate cancer is characterized by an uncontrolled proliferation of prostate cells which can invade and destroy adjacent tissues as well as metastasize. Primary prostate tumors can be classified into stages TX, T0, T1, T2, T3, and T4 and metastatic tumors can be classified into stages D1, D2 and D3. Similarly, there are classifications known by those skilled in the art for the progressive stages of precancerous lesions or PIN. The methods herein are applicable for the diagnosis or treatment of any or all stages of prostate neoplastic conditions, other than benign prostatic hypertrophy. In one embodiment, the method for diagnosing or predicted susceptibility to a prostate neoplastic condition does not include diagnosing or predicted susceptibility to benign prostatic hypertrophy.

The use of a level of a biomarker, such as RDC1 or another biomarker having a nucleotide sequence listed by GenBank accession number in Table 1, in prostate cells, the circulatory system and urine as a diagnostic indicator of a prostate pathology, allows for early diagnosis as a predictive indicator when no physiological or pathological symptoms are apparent. The methods are applicable to any males over age 50, African-American males and males with familial history of prostate neoplastic conditions or pathologies. The diagnostic methods of the invention also are applicable to individuals predicted to be at risk for prostate neoplastic conditions or pathologies by reliable prognostic indicators prior to onset of overt clinical symptoms. Those skilled in the art will know by using routine examinations and practices in the field of medicine those individuals who are applicable candidates for diagnosis by the methods of the invention.

For example, individuals suspected of having a prostate neoplastic condition can be identified by exhibiting presenting signs of prostate cancer which include, for example, a palpable nodule (>50% of the cases), dysuria, cystitis and prostatitis, frequency, urinary retention, or decreased urine stream. Signs of advanced disease include pain, uremia, weight loss and systemic bleeding. Prognostic methods of this invention are applicable to individuals after diagnosis of a prostate neoplastic condition, for example, to monitor improvements or identify residual neoplastic prostate cells using, for example, imaging methods known in the art and which target RDC1 or another biomarker having a nucleotide or amino acid sequence referenced by GenBank accession number in Table 1.

The diagnostic methods of the invention are applicable for use with a variety of different types of samples isolated or obtained from an individual having, or suspected of having, a prostate neoplastic condition or prostate pathology. For example, samples applicable for use in one or more diagnostic formats of the invention include tissue and cell samples. A tissue or cell sample can be obtained, for example, by biopsy or surgery. As described below, and depending on the format of the method, the tissue can be used whole or subjected to various methods known in the art to disassociate the sample into smaller pieces, cell aggregates or individual cells. Additionally, when combined with amplification methods such as polymerase chain reaction (PCR), a single prostate cell sample is sufficient for use in diagnostic assays of the invention that employ hybridization detection methods. Similarly, when measuring biomarker polypeptide levels, amplification of the signal with enzymatic coupling or photometric enhancement can be employed using only a few or a small number of cells.

Whole tissue obtained from a prostate biopsy or surgery is one example of a prostate cell sample. Whole tissue prostate cell samples can be assayed employing any of the formats described below. For example, the prostate tissue sample can be mounted and hybridized in situ with biomarker nucleic acid probes. Similar histological formats employing protein detection methods and in situ activity assays also can be used to detect biomarker polypeptides in whole tissue prostate cell samples. Protein detection methods include, for example, staining with biomarker specific antibodies. Such histological methods as well as others well known to those skilled in the art are applicable for use in the diagnostic methods of the invention using whole tissue as the source of a prostate cell sample. Methods for preparing and mounting the samples are similarly well known in the art.

Individual prostate cells and cell aggregates from an individual having, or suspected of having, a prostate neoplastic condition is another example of a prostate cell sample that can be analyzed for increased expression of biomarker RNA or polypeptide. The cells can be grown in culture and analyzed in situ using procedures such as those described above. Generally, however, whole cell samples expressing cell surface markers such as RDC1 can be rapidly tested using fluorescent or magnetic activated cell sorting (FACS or MACS) with labeled binding agents specific for a biomarker, such as RDC1, or using binding agents selective for epithelial or prostate cell populations, for example, and then determining the level of a biomarker within this population. The level can be determined by, for example, binding agents specific for a biomarker, such as RDC1, or by hybridization to a biomarker specific probe. Other methods for measuring the level of a biomarker in whole cell samples are known in the art and are similarly applicable in any of the diagnostic formats described below.

The tissue or whole cell prostate cell sample obtained from an individual also can be analyzed for increased biomarker expression by lysing the cell and measuring the expression levels of a biomarker in the lysate, a fractionated portion thereof or a purified component thereof using any of diagnostic formats described below. For example, if a hybridization format is used, biomarker RNA can be amplified directly from the lysate using PCR, or other amplification procedures well known in the art such as RT-PCR, 5' or 3' RACE to directly measure the expression level of the biomarker. RNA also can be isolated and probed directly such as by solution hybridization or indirectly by hybridization to immobilized RNA. Similarly, when determining the level of a biomarker using polypeptide detection formats, lysates can be assayed directly, or they can be further fractionated to enrich for the biomarker. Numerous other methods applicable for use with whole prostate cell samples are well known to those skilled in the art and can accordingly be used in the methods of the invention.

The prostate tissue or cell sample can be obtained directly from the individual or, alternatively, it can be obtained form other sources for testing. Similarly, the cell sample can be tested when it is freshly isolated or it can be tested following short or prolonged periods of cryopreservation without substantial loss in accuracy or sensitivity. If the sample is to be tested following an indeterminate period of time, it can be obtained and then cryopreserved, or stored at 4° C. for short periods of time, for example. An advantage of the diagnostic methods of the invention is that they do not require histological analysis of the sample. As such, the sample can be initially disaggregated, lysed, fractionated or purified and the active component stored for later diagnosis.

A soluble portion of a biomarker that has an extracellular region, such as RDC1, can be cleaved, and become present in a bodily fluid of an individual. Therefore, fluid samples which can be measured for biomarker levels include, for example, blood, serum, lymph, urine and semen. Other bodily fluids are known to those skilled in the art and are similarly applicable for use as a sample in the diagnostic methods of the invention. One advantage of analyzing fluid samples is that they are readily obtainable, in sufficient quantity, without invasive procedures as required by biopsy and surgery. Analysis of fluid samples such as blood, serum and urine will generally be in the diagnostic formats described above and biomarker polypeptide is circulating in a soluble form, the methods will be similar to those which measure levels from cell lysates, fractionated portions thereof or purified components.

Given the teachings and guidance provided herein, the choice of measuring RNA or polypeptide levels will be that of the user. Considerations such as the sample type, availability and amount will also influence selection of a particular diagnostic format. For example, if the sample is a prostate cell sample and there is only a small amount available, then diagnostic formats which measure the amount of biomarker RNA, by, for example, PCR amplification, or which measure biomarker cell surface polypeptides by, for example, FACS analysis can be appropriate choices for determining the level of biomarker. Alternatively, if the sample is a blood sample and the user is analyzing numerous different samples simultaneous, such as in a clinical setting, then a multisample format, such as an Enzyme Linked Immunoabsorbant Assay (ELISA), which measures the amount of biomarker polypeptide can be an appropriate choice for determining the level of biomarker. Additionally, biomarker nucleic acids released into bodily fluids from the neoplastic or pathological prostate cells can also be analyzed by, for example, PCR or RT-PCR. Those skilled in the art will know, or can determine which format is amenable for a particular application and which methods or modifications known within the art are compatible with a particular type of format.

Hybridization methods are applicable for measuring the amount of biomarker RNA as an indicator of biomarker nucleic acid levels. There are numerous methods well known in the art for detecting nucleic acids by specific or selective hybridization with a complementary probe. Such methods include both solution hybridization procedures and solid-phase hybridization procedures where the probe or sample is immobilized to a solid support. Descriptions for such methods can be found in, for example, Sambrook et al., *Molecular Cloning: A Laboratory Manual*, 3rd ed., Cold Spring Harbor Press, Cold Spring Harbor, N.Y. (2001). Specific examples of such methods include PCR and other amplification methods such as RT-PCR, 5' or 3' RACE, RNase protection, RNA blot, dot blot or other membrane-based technologies, dip stick, pin, ELISA or two-dimensional arrays immobilized onto chips as a solid support. These methods can be performed using either qualitative or quantitative measurements, all of which are well known to those skilled in the art.

PCR or RT-PCR can be used with isolated RNA or crude cell lysate preparations. As described previously, PCR is advantageous when there is little starting material. A further description of PCR methods can be found in, for example, Dieffenbach, C. W., and Dveksler, G. S., *PCR Primer: A Laboratory Manual*, Cold Spring Harbor Press, Plainview, N.Y. (1995). Multisample formats such as an ELISA or two-dimensional array offer the advantage of analyzing numerous, different samples in a single assay. Solid-phase dip stick-based methods offer the advantage of being able to rapidly analyze a patient's fluid sample and obtain an immediate result.

Nucleic acid probes useful for measuring the level of biomarker by hybridization include, for example, nucleic acids corresponding to a nucleic acid molecule referenced by accession number in Table 1, or an RDC1 nucleic acid sequence, such as that referenced as SEQ ID NO:1, and oligonucleotides therefrom, corresponding to biomarker nucleotide sequences capable of specifically hybridizing to the corresponding biomarker RNA. Such oligonucleotides can contain at least 15 contiguous nucleotides from the reference nucleotide sequence, can include at least 16, 17, 18, 19, 20 or at least 25 contiguous nucleotides, and often includes at least 30, 40, 50, 60, 70, 80, 90, 100, 125, 150, 175, 200, 225, 250, 275, 300, 325, up to 350 contiguous nucleotides from the reference nucleotide sequence. Those skilled in the art are able to access the public sequence database GenBank to obtain the nucleotide sequence of a biomarker useful in a method of the invention because GenBank accession numbers are listed in Table 1. Those skilled in the art will be able to select a probe sequence from any nucleotide sequence corresponding to a biomarker useful in a method of the invention. A variety of well known computer programs can be used for probe selection, if desired. Such programs include, for example, OSP(*PCR Methods and Applications* 1:124-128 (1991)) and PCAP (*Comput. Appl. Biosci.* 9:201-203 (1993)).

Briefly, for detection by hybridization, the biomarker nucleic acid probes having detectable labels are added to a prostate cell sample or a fluid sample obtained from the individual having, or suspected of having, a prostate neoplastic condition under conditions which allow annealing of the probe to the corresponding biomarker RNA. Such conditions are well known in the art for both solution and solid phase hybridization procedures. Moreover, optimization of hybridization conditions can be performed, if desired, by hybridization of an aliquot of the sample at different temperatures, durations and in different buffer conditions. Such procedures are routine and well known to those skilled. Following annealing, the sample can be washed and the signal measured and compared with a reference or standard value. The magnitude of the hybridization signal is directly proportional to the expression level of the particular biomarker.

Essentially all modes of affinity binding assays are applicable for use in determining a level of a biomarker in a sample. Such methods are rapid, efficient and sensitive. Moreover, affinity binding methods are simple and can be modified to be performed under a variety of clinical settings and conditions to suit a variety of particular needs. Affinity binding assays that are known and can be used in the methods of the invention include both soluble and solid phase formats. A specific example of a soluble phase affinity binding assay is immunoprecipitation using a biomarker selective antibody or other binding agent. Solid phase formats are advantageous for the methods of the invention since they are rapid and can be performed more easily on multiple different samples simultaneously without losing sensitivity or accuracy. Moreover, solid phase affinity binding assays are further amenable to high throughput screening and automation.

Specific examples of solid phase affinity binding assays include immunohistochemical binding assays, immunoaffinity binding assays such as an ELISA and radioimmune assay (RIA). Other solid phase affinity binding assays are known to those skilled in the art and are applicable to the methods of the invention. Although affinity binding assays are generally formatted for use with an antibody binding molecules that is selective for the analyte or ligand of interest, essentially any binding agent can be alternatively substituted for the selectively binding antibody. Such binding agents include, for example, macromolecules such as polypeptides, peptides, nucleic acid molecules, lipids and sugars as well as small molecule compounds. Methods are known in the art for identifying such molecules which bind selectively to a particular analyte or ligand and include, for example, surface display libraries and combinatorial libraries. Thus, for a molecule other than an antibody to be used in an affinity binding assay, all that is necessary is for the binding agent to exhibit selective binding activity for a biomarker.

The various modes of affinity binding assays, such as immunoaffinity binding assays, include, for example, immunohistochemistry methods, solid phase ELISA and RIA as well as modifications thereof. Such modifications thereof include, for example, capture assays and sandwich assays as well as the use of either mode in combination with a competition assay format. The choice of which mode or format of immunoaffinity binding assay to use will depend on the intent of the user. Such methods can be found described in common laboratory manuals such as Harlow and Lane, *Using Antibodies: A Laboratory Manual*, Cold Spring Harbor Laboratory Press, New York (1999).

An antibody useful in the methods of the invention includes a polyclonal and monoclonal antibody, as well as an antigen binding fragment of such antibodies. Methods of preparing polyclonal or monoclonal antibodies are well known to those skilled in the art and are described, for example, in Harlow and Lane, *Antibodies: A Laboratory Manual*, Cold Spring Harbor Laboratory Press (1988).

An antibody useful in the methods of the invention also includes naturally occurring antibodies as well as non-naturally occurring antibodies, including, for example, single chain antibodies, chimeric, bifunctional and humanized antibodies, as well as antigen-binding fragments thereof. Such non-naturally occurring antibodies can be constructed using solid phase peptide synthesis, can be produced recombinantly or can be obtained, for example, by screening combinatorial libraries consisting of variable heavy chains and variable light chains as described by Huse et al. (*Science* 246:1275-1281 (1989)). These and other methods of making, for example, chimeric, humanized, CDR-grafted, single chain, and bifunctional antibodies are well known to those skilled in the art (Winter and Harris, *Immunol. Today* 14:243-246 (1993); Ward et al., *Nature* 341:544-546 (1989); Harlow and Lane, supra, 1988); Hilyard et al., *Protein Engineering: A practical approach* (IRL Press 1992); Borrabeck, *Antibody Engineering*, 2d ed. (Oxford University Press 1995)).

Formats employing affinity binding can be used in conjunction with a variety of detection labels and systems known in the art to quantitate amounts of biomarkers in the analyzed sample. Detection systems include the detection of bound biomarker by both direct and indirect means. Direct detection methods include labeling of the biomarker-specifically reactive antibody or binding agent. Indirect detection systems include, for example, the use of labeled secondary antibodies and binding agents.

Secondary antibodies, labels and detection systems are well known in the art and can be obtained commercially or by techniques well known in the art. The detectable labels and systems employed with the biomarker-selective binding agent should not impair binding of the agent to the biomarker. Moreover, multiple antibody and label systems can be employed for detecting the bound biomarker-specifically reactive antibody to enhance the sensitivity of the binding assay if desired.

Detectable labels can be essentially any label that can be quantitated or measured by analytical methods. Such labels include, for example, enzymes, radioisotopes, fluorochromes as well as chemilluminescent and bioluminescent compounds. Specific examples of enzyme labels include horseradish peroxidase (HRP), alkaline phosphatase (AP), (β-galactosidase, urease and luciferase.

A horseradish-peroxidase detection system can be used, for example, with the chromogenic substrate tetramethylbenzidine (TMB), which yields a soluble product in the presence of hydrogen peroxide that is detectable by determining absorbance at 450 nm. An alkaline phosphatase detection system can be used with the chromogenic substrate p-nitrophenyl phosphate, for example, which yields a soluble product readily detectable by determining absorbance at 405 nm. Similarly, a β-galactosidase detection system can be used with the chromogenic substrate o-nitrophenyl-β-D-galactopyranoside (ONPG), which yields a soluble product detectable by determining absorbance at 410 nm, or a urease detection system can be used with a substrate such as urea-bromocresol purple (Sigma Immunochemicals, St. Louis, Mo.). Luciferin is the substrate compound for luciferase which emits light following ATP-dependent oxidation.

Fluorochrome detection labels are rendered detectable through the emission of light of ultraviolet or visible wavelength after excitation by light or another energy source. DAPI, fluorescein, Hoechst 33258, R-phycocyanin, B-phycoerythrin, R-phycoerythrin, rhodamine, Texas red and lissamine are specific examples of fluorochrome detection labels that can be utilized in the affinity binding formats of the invention. A particularly useful fluorochrome is fluorescein or rhodamine.

Chemiluminescent as well as bioluminescent detection labels are convenient for sensitive, non-radioactive detection of a biomarker and can be obtained commercially from various sources such as Amersham Lifesciences, Inc. (Arlington Heights, Ill.).

Alternatively, radioisotopes can be used as detectable labels in the methods of the invention. Iodine-125 is a specific example of a radioisotope useful as a detectable label.

Signals from detectable labels can be analyzed, for example, using a spectrophotometer to detect color from a chromogenic substrate; a fluorometer to detect fluorescence in the presence of light of a certain wavelength; or a radiation counter to detect radiation, such as a gamma counter for detection of iodine-125. For detection of an enzyme-linked secondary antibody, for example, a quantitative analysis of the amount of bound agent can be made using a spectrophotometer such as an EMAX Microplate Reader (Molecular Devices, Menlo Park, Calif.) in accordance with the manufacturer's instructions. If desired, the assays of the invention can be automated or performed robotically, and the signal from multiple samples can be detected simultaneously.

Assay formats useful in the present invention can be forward, reverse or simultaneous as described in U.S. Pat. No. 4,376,110 and No. 4,778,751. Separation steps for the various assay formats described herein, including the removal of unbound secondary antibody, can be performed by methods known in the art (Harlow and Lane, supra). For example, washing with a suitable buffer can be followed by filtration, aspiration, vacuum or magnetic separation as well as by centrifugation.

A binding agent selective for a biomarker also can be used in imaging methods that are targeted at biomarker-expressing neoplastic cells. These imaging techniques will have utility in identification of residual neoplastic cells at the primary site following standard treatments including, for example, surgical resection of an organ of the gastrointestinal system, such as the colon, and radiation therapy. In addition, imaging techniques that detect neoplastic cells have utility in detecting secondary sites of metastasis. The biomarker specific binding agent can be radiolabeled with, for example, indium and infused intravenously as described by Kahn et al., *Journal of Urology* 152:1952-1955 (1994). The binding agent selective for a biomarker can be, for example, a monoclonal antibody specifically reactive with a biomarker such as an angrogen-regulated gene. Imaging can be accomplished by, for example, radioimmunoscintigraphy as described by Kahn et al., supra.

The reference level of a biomarker can be determined by a plurality of methods. The reference level can be determined by, for example, determining the level of a biomarker in non-neoplastic cells from the same tissue type as the tissue of cells to be tested, such as prostate tissue. As another example, the reference level can be determined by determining the level of a biomarker in androgen-dependent tissue when the biomarker is being used to diagnose or determine a prognosis for androgen-independent prostate cancer.

When the level of a biomarker in a sample from an individual is 2-fold or more higher than the normal reference level of the biomarker, the cells are considered to have a high level of, or overproduction, of the biomarker, which is correlated with a prostate neoplastic condition such as cancer. Similarly, when the level of a biomarker in sample from an individual is 2-fold or more lower than the disease-state reference level, the cells are considered to have a low level of, or underproduction, of the biomarker, which is correlated with a normal condition.

The reference level also can be determined by comparison of the level of a biomarker in populations of individuals having the same cancer. This can be accomplished, for example, by histogram analysis, in which an entire cohort of patients are graphically presented, wherein a first axis represents the level of the biomarker, and a second axis represents the number of patients in the cohort whose neoplastic cells express the biomarker at a given level. Two or more separate groups of patients can be determined by identification of subsets populations of the cohort which have the same or similar levels of the biomarker. Determination of the reference level can then be made based on a level which best distinguishes these separate groups. A reference level also can represent the levels of two or more markers. Two or more markers can be represented, for example, by a ratio of values for levels of each biomarker.

The reference level can be a single number, equally applicable to every individual, or the reference level can vary, according to specific subpopulations of individuals. For example, older men might have a different reference level than younger men for the same cancer. Furthermore, the reference level can be some level determined for each patient individually. For example, the reference level can be a certain ratio of a biomarker in the neoplastic cells of a patient relative to the biomarker levels in non-tumor cells within the same patient. Thus the reference level for each patient can be proscribed by a reference ratio of one or more biomarkers, where the reference ratio can be determined by any of the methods for determining the reference levels described herein.

A high level of a biomarker, or overproduction of a biomarker gene, is related to a level of the biomarker above a determined reference level. Thus, a reference level of a biomarker in a cell is identified as a "cutoff" value, above which there is a significant correlation between the presence of the biomarker and increased or decreased likelihood of the sample containing tumor cells. Those of skill in the art will recognize that some "cutoff" values are not sharp in that clinical correlations are still significant over a range of values on either side of the cutoff; however, it is possible to select an optimal cutoff value (for example varying H-scores, and the like) of a level of a biomarker for a cancer cell type. It is understood that improvements in optimal cutoff values could be determined, depending on the sophistication of statistical methods used and on the number and source of samples used to determine reference or basal values.

Such overproduction is not typically calculated in terms of absolute biomarker levels, but is determined using relative measurements. These relative measurements are illustrated for quantitation purposes with an internal standard; however, it will be appreciated that other standards or methods of determination can be used, such as comparison with external standards, biomarker polypeptide measurements, biomarker mRNA measurements, absolute values of protein, mRNA or DNA levels, and the like.

A reference level can also be determined by comparison of biomarker levels in populations of individuals having cancer, such as patients having cancer of the same stage. This can be accomplished by histogram analysis, in which the entire cohort of patients tested are graphically presented, wherein a first axis represents the level of a biomarker, and a second axis represents the number of patients in the cohort whose tumor cells contain the biomarker at a given level. Two or more separate groups of patients can be determined by identification of subsets populations of the cohort which have the same or similar levels of the biomarker. Determination of the reference level can then be made based on a biomarker level that best distinguishes these separate groups.

Verification that the reference level distinguishes the likelihood of neoplastic cell presence in a sample from individuals expressing below-reference biomarker levels versus individuals expressing above-reference biomarker levels can be carried out using single variable or multi-variable analysis. These methods determine the likelihood of a correlation between one or more variables and a given outcome. In the specific case, the methods will determine the likelihood of a correlation between a biomarker levels (or biomarker level coupled with another variable) and presence of a prostate neoplastic condition in an individual. Any one of a plurality of methods well known to those of ordinary skill in the art for carrying out these analyses can be used. Examples of single variable analysis is the Kaplan-Meir method or the log-rank test. An example of multi-variable analysis is the Cox proportional-hazards regression model. Population-based determination of reference levels, for example, by histogram analysis can be carried out using a cohort of patients sufficient in size in order to determine two or more separate groups of patients having different biomarker levels.

Further, while a reference level can separate two groups of individuals, it is within the scope of the invention that numerous reference values might exist which separate a plurality of populations. For example, two reference values can separate a first group of individuals with high levels of a biomarker from a second group of individuals with intermediate levels the biomarker, and from a third group of individuals with low levels of the biomarker. The number of different reference levels can be sufficient to proscribe a curve, such as a continuous line, which describes the likelihood of the presence of a prostate neoplastic condition in an individual as a function of the biomarker level in that individual. Such a curve will constitute a "continuous" biomarker level, where the likelihood of the presence of a prostate neoplastic condition in an individual is proportional to the biomarker level in that individual. Two or more biomarker levels also can be represented by such a curve.

The reference level of a biomarker can further be used in conjunction with another variable found to be a statistically significant indicator of a prostate neoplasitic condition in an individual. Such indicators include the presence or levels of known cancer markers, or can be clinical or pathological indicators (for example, age, tumor size, tumor histology, clinical stage, family history and the like).

A difference between a level of expression of an androgen-regulated gene used as a biomarker in test sample, such as RDC1, versus a reference level can be determined manually (by a person) or by a computer or other machine. An algorithm can be used to detect differences between a test sample level of a biomarker and a reference level. The algorithm can score and compare, for example, differences in intensity of expression of a particular biomarker and score changes in intensity between two samples. A variety of such algorithms are known in the art. Differences are considered significant when they are 2-fold or greater, 3-fold or greater or 5-fold or greater. Alternatively, a mathematical approach can be used to conclude whether differences in biomarker levels in two or more sample is significant (see, for example, Golub et al., *Science* 286:521 (1999)). One approach to determine whether a sample is more similar to or has maximum similarity with a given condition, such as a particular stage of tumor progression) is to compare the Euclidean distances between the sample and one or more pools representing different conditions for comparison; the pool with the smallest vector angle is then selected as the more similar to the test sample among the pools compared.

The diagnostic procedures described above and below can additionally be used in conjunction with other prostate markers, such as other prostate androgen-regulated genes, prostate specific antigen, human glandular kallikrein 2 (hk2) and prostase/PRSS18 for simultaneous or independent corroboration of a sample. Additionally, biomarker expression can be used in conjunction with smooth muscle cell markers to distinguish between pathological conditions such as neoplasia and malignant prostate cancer. The use of a combination of an androgen-regulated gene, such as RDC1, with one or more other biomarkers, including those referenced in Table 1, can provide increased diagnostic significance or confidence in a diagnostic or prognostic determination. Those skilled in the art will know which markers are applicable for use in conjunction with RDC1 or a biomarker listed in Table 1 to delineate more specific diagnostic information such as that described above.

As shown herein, RDC1 polypeptide levels are reduced in prostate cancer cells treated with androgen, and RDC1 has an important role in maintaining a proliferative phenotype of such androgen-treated cells. Therefore, a compound that decreases the activity of RDC1 is a potential therapeutic compound for decreasing the ability of prostate cancer cells to proliferate. Thus, the invention provides a method for screening for a compound for decreasing prostate cell growth. The method involves (a) contacting a compound that is a RDC1 antagonist with a cell; and (b) determining a proliferation state of the cell, wherein a compound that reduces proliferation of the cell is identified as a compound that decreases prostate cell growth.

A variety of well-known assays can be used to identify an RDC1 antagonist. Such assays include methods for identifying GPCR antagonists in the presence of a ligand, as well as methods for identifying GPCR antagonists in the absence of a ligand. An exemplary assay that employs an RDC1 ligand involves contacting RDC1 with one or more candidate compounds under conditions wherein an RDC1 ligand promotes a predetermined signal and identifying a compound that reduces the predetermined signal. Another exemplary assay for identifying an RDC1 antagonist involves contacting RDC1 with one or more candidate compounds in the presence of a RDC1 agonist or ligand under conditions wherein the agonist or ligand binds to RDC1 and identifying a compound that reduces the binding. An RDC1 ligand or agonist for use in such assays can be, for example, adrenomedullin, a chemokine or another substance that binds to and activates RDC1. An exemplary assay for identifying an RDC1 antagonist in the absence of a ligand or agonist is referred to as Constitutively Activated Receptor Technology (CART), and is described, for example, at the URL arenapharm.com. Other assays for identifying a GPCR antagonist in the absence of a ligand are known to those skilled in the art.

A variety of in vitro screening methods are useful for identifying a RDC1 antagonist. The ability of a compound to modulate RDC1 can be indicated, for example, by the ability to block agonist binding to RDC1 or reduce a predetermined signal produced by a RDC1. Therefore, signaling and binding assays can be used to identify a RDC1 antagonist.

An RDC1 antagonist is a compound that selectively inhibits or decreases normal signal transduction through the RDC1. An RDC1 antagonist can act by any antagonistic mechanism, such as by binding a RDC1 or a ligand, thereby inhibiting binding between RDC1 and the ligand. A RDC1 antagonist can also inhibit binding between a specific or non-specific RDC1 agonist. An RDC1 antagonist can also act, for example, by inhibiting the binding activity of a ligand or signaling activity of RDC1.

A predetermined signal is a readout, detectable by any analytical means, that is a qualitative or quantitative indication of activation of G-protein-dependent signal transduction through RDC1. Assays used to determine such qualitative or quantitative activation of G-protein-dependent signal transduction through RDC1, are referred to below as "signaling assays."

Signaling through G proteins can lead to increased or decreased production or liberation of second messengers, including, for example, arachidonic acid, acetylcholine, diacylglycerol, cGMP, cAMP, inositol phosphate, such as inositol-1,4,5-trisphosphate, and ions, including $Ca^{++}$ ions; altered cell membrane potential; GTP hydrolysis; influx or efflux of amino acids; increased or decreased phosphorylation of intracellular proteins; or activation of transcription.

Various assays, including high throughput automated screening assays, to identify alterations in G-protein coupled signal transduction pathways are well known in the art. Various screening assay that measure $Ca^{++}$, cAMP, voltage changes and gene expression are reviewed, for example, in Gonzalez et al., *Curr. Opin. in Biotech.* 9:624-631 (1998); Jayawickreme et al., *Curr. Opin. Biotech.* 8:629-634 (1997); and Coward et al., *Anal. Biochem.* 270:2424-248 (1999). Yeast cell-based bioassays for high-throughput screening of drug targets for G-protein coupled receptors are described, for example, in Pausch, *Trends in Biotech.* 15:487-494 (1997). A variety of cell-based expression systems, including bacterial, yeast, baculovirus/insect systems and mammalian cells, useful for detecting G-protein coupled receptor agonists and antagonists are reviewed, for example, in Tate et al., *Trends in Biotech.* 14:426-430 (1996).

Assays to detect and measure G-protein-coupled signal transduction can involve first contacting a sample containing RDC1, such as an isolated cell, membrane or artificial membrane, such as a liposome or micelle, with a detectable indicator. A detectable indicator can be any molecule that exhibits a detectable difference in a physical or chemical property in the presence of the substance being measured, such as a color change. Calcium indicators, pH indicators, and metal ion indicators, and assays for using these indicators to detect and measure selected signal transduction pathways are described, for example, in Haugland, *Molecular Probes Handbook of Fluorescent Probes and Research Chemicals*, Sets 20-23 and 25 (1992-94). For example, calcium indicators and their use are well known in the art, and include compounds like Fluo-3 AM, Fura-2, Indo-1, FURA RED, CALCIUM GREEN, CALCIUM ORANGE, CALCIUM CRIMSON, BTC, OREGON GREEN BAPTA, which are available from Molecular Probes, Inc., Eugene Oreg., and described, for example, in U.S. Pat. Nos. 5,453,517, 5,501,980 and 4,849,362.

The specificity of a G-protein for cell-surface receptors is determined by the C-terminal five amino acids of the Gα subunit. The nucleotide sequences and signal transduction pathways of different classes and subclasses of Gα subunits in a variety of eukaryotic and prokaryotic organisms are well known in the art. Thus, any convenient G-protein mediated signal transduction pathway can be assayed by preparing a chimeric Gα containing the C-terminal residues of a Gα that couples to RDC1, such as Gαq, with the remainder of the protein corresponding to a Gα that couples to the signal transduction pathway it is desired to assay. Methods of recombinantly expressing chimeric Gα proteins are known in the art and are described, for example, in Conklin et al., *Nature* 363:274-276 (1993), Komatsuzaki et al., *FEBS Letters* 406:165-170 (1995), and Saito et al., *Nature* 400:265-269 (1999). Additionally, chimeric Gα proteins can be prepared by synthetic methods.

A binding assay can be performed to identify compounds that are RDC1 antagonists. In such an assay, RDC1 can be contacted one or more candidate compounds under conditions in which RDC1 binds to the selected receptor and a compound that binds to the selected receptor or that reduces binding of an agonist to selected receptor can be identified. Contemplated binding assays can involve detectably labeling a candidate compound, or competing an unlabeled candidate compound with a detectably labeled RDC1 agonist, such as adrenomedulin. A detectable label can be, for example, a radioisotope, fluorochrome, ferromagnetic substance, or luminescent substance. Exemplary radiolabels useful for labeling compounds include 125I, 14C and 3H. Methods of detectably labeling organic molecules, either by incorporating labeled amino acids into the compound during synthesis, or by derivatizing the compound after synthesis, are known in the art.

An exemplary assay for determining binding of detectably labeled adrenomedullin to RDC1 is the radioligand filter binding assay described in Li et al. *Molecular Pharmacology* 59:692-698 (2001)). A variety of other low- and high-throughput assays suitable for detecting selective binding interactions between a receptor and a ligand are known in the art. Such assays include, for example, fluorescence correlation spectroscopy (FCS) and scintillation proximity assays (SPA) reviewed in Major, *J. Receptor and Signal Transduction Res.* 15:595-607 (1995); and in Sterrer et al., *J. Receptor and Signal Transduction Res.* 17:511-520 (1997)). Binding assays can be performed in any suitable assay format including, for example, cell preparations such as whole cells or membranes that contain RDC1, or substantially purified RDC1, either in solution or bound to a solid support.

Assay methods for identifying compounds that selectively bind to or modulate signaling through a RDC1 generally involve comparison to a control. One type of a "control" is a preparation that is treated identically to the test preparation, except the control is not exposed to the candidate compound. Another type of "control" is a preparation that is similar to the test preparation, except that the control preparation does not express the receptor, or has been modified so as not to respond selectively to a ligand. In this situation, the response of the test preparation to a candidate compound is compared to the response (or lack of response) of the control preparation to the same compound under substantially the same reaction conditions.

An RDC1 used in the screening methods of the invention can be, for example, a mouse, rat or human RDC1, including a recombinantly produced receptor or naturally occurring receptor present in a cell preparation.

The screening methods of the invention can involve contacting RDC1 with a candidate compound. A candidate compound used in the screening methods of the invention can be a naturally occurring macromolecule, such as a peptide, nucleic acid, carbohydrate, lipid, or any combination thereof. A candidate compound also can be a partially or completely synthetic derivative, analog or mimetic of such a macromolecule, or a small organic or inorganic molecule prepared partly or completely by combinatorial chemistry methods.

A candidate compound further can be an antibody, including a monoclonal, humanized and chimeric antibodies, and functional fragments of an antibody includes chimeric, bifunctional, humanized and single chain antibodies (scFv), variable region fragments (Fv or Fd), Fab and F(ab)2. An antibody can be naturally occurring or non-naturally occurring.

A candidate compound that is a nucleic acid can include, for example, an anti-sense nucleotide sequence, an RNA molecule, or an aptamer sequence. An anti-sense nucleotide sequence can bind to a nucleotide sequence within a cell and modulate the level of expression of a biomarker gene, or modulate expression of another gene that controls the expression of the biomarker. Similarly, an RNA molecule, such as a catalytic ribozyme, can bind to and alter the expression of an androgen-regulated gene, or other gene that controls the expression of an androgen-regulated gene. An aptamer is a nucleic acid sequence that has a three dimensional structure capable of binding to a molecular target, such as an androgen-regulated gene (Jayasena, S. D. *Clinical Chemistry* 45:1628-1650 (1999)).

A candidate compound that is a nucleic acid also can be a double-stranded RNA molecule for use in RNA interference methods. RNA interference (RNAi) is a process of sequence-specific gene silencing by post-transcriptional RNA degradation, which is initiated by double-stranded RNA (dsRNA) homologous in sequence to the silenced gene. A suitable double-stranded RNA (dsRNA) for RNAi contains sense and antisense strands of about 21 contiguous nucleotides corresponding to the gene to be targeted that form 19 RNA base pairs, leaving overhangs of two nucleotides at each 3' end (Elbashir et al., *Nature* 411:494-498 (2001); Bass, *Nature* 411:428-429 (2001); Zamore, *Nat. Struct. Biol.* 8:746-750 (2001)). dsRNAs of about 25-30 nucleotides have also been used successfully for RNAi (Karabinos et al., *Proc. Natl. Acad. Sci.* 98:7863-7868 (2001). dsRNA can be synthesized in vitro and introduced into a cell by methods known in the art.

The methods of the invention can include screening candidate compounds to identify a compound that decreases cell growth. The number of different candidate compounds to screen in a particular assay can be determined by those skilled in the art, and can be 2 or more, such as 5, 10, 15, 20, 50 or 100 or more different compounds. For certain applications, such as when a library of random compounds is to be screened, and for automated procedures, it can be desirable to screen 103 or more compounds, such as 105 or more compounds, including 107 or more compounds.

Compounds for screening can be contained within large libraries of compounds, such as when high-throughput in vitro screening formats are used. Methods for producing large libraries of chemical compounds, including simple or complex organic molecules, metal-containing compounds, carbohydrates, peptides, proteins, peptidomimetics, glycoproteins, lipoproteins, nucleic acids, antibodies, and the like, are well known in the art and are described, for example, in Huse, U.S. Pat. No. 5,264,563; Francis et al., *Curr. Opin. Chem. Biol.* 2:422-428 (1998); Tietze et al., *Curr. Biol.,* 2:363-371 (1998); Sofia, *Mol. Divers.* 3:75-94 (1998); Eichler et al., *Med. Res. Rev.* 15:481-496 (1995); and the like. Libraries containing large numbers of natural and synthetic compounds also can be obtained from commercial sources.

Compounds can be screened individually or in pools of a few, tens or hundreds of compounds. Therefore, a library of compounds can be screened sequentially, in a multi-sample format, in which each sample receives one compound, or multiplexed format, in which each sample receives more than one compound.

An RDC1 antagonist can be contacted with a cell contained in a cell preparation, tissue, organ, organism or animal that has at least one observable index of proliferation and expresses RDC1. The ability of the RDC1 antagonist to modulate cell growth can be tested in a variety of animal species, as well as organs, tissues, and cells obtained from such animals, and cell preparations derived therefrom.

The ability of an RDC1 antagonist to decrease proliferation of a cell can be determined by treating the cell with the compound and observing or measuring the proliferation state of the cell in comparison to a control condition. The proliferation state of a cell can be determined by growth rate, a gene expression pattern correlated with growth, a physical characteristic of a cell correlated with growth, such as reduced adherence and the like. As such, the effect of an RDC1 antagonist on a prostate neoplastic or cancer cell can be assessed by several criteria well known in the art. For example, a neoplastic or cancer cell can be distinguished from a normal cell by the uncontrolled growth and invasive properties characteristic of cancer cells. Using histological methods, a cancer cell can be observed to invade into surrounding normal tissue, have an increased mitotic index, and increased nuclear to cytoplasmic ratio, altered deposition of extracellular matrix, and a less differentiated phenotype. The unregulated proliferation of a cancer cell can be characterized by anchorage independent cell growth, proliferation in reduced-serum medium, loss of contact inhibition, and rapid proliferation compared to normal cells. Those skilled in the art will know how to determine if an RDC1 antagonist is effective in promoting a more normal phenotype in a cancer cell. Those skilled in the art will also be able to detect a cancer cell in a population of cells, tumor, or organ.

Animal models of hyperproliferative diseases similarly can be used to assess the activity of an RDC1 antagonist. Such animal tumor models can be predictive of the therapeutic efficacy of a an RDC1 antagonist used to decrease proliferation. These models generally include the inoculation or implantation of a laboratory animal with heterologous tumor cells followed by simultaneous or subsequent administration of a therapeutic treatment. The efficacy of the treatment is determined by measuring the extent of tumor growth or metastasis. Measurement of clinical or physiological indicators can alternatively or additional be assessed as an indicator of treatment efficacy. Exemplary animal tumor models can be found described in, for example, Brugge et al. *Origins of Human Cancer*, Cold Spring Harbor Laboratory Press, Plain View, N.Y., (1991).

Because an RDC1 antagonist can function to decrease androgen-independent prostate cell growth, the invention provides a method for reducing prostate cell growth in a mammal. The method involves administering to the mammal an effective amount of a RDC1 antagonist. The RDC1 antagonist can be used to treat a prostate neoplastic condition in an individual, including prostate cancer such as androgen-independent prostate cancer.

RDC1 and the other biomarkers having nucleotide sequences referenced by GenBank accession number in Table 1 can be over-expressed in androgen-independent prostate cells. Therefore, the invention further provides a method for targeting a therapeutic moiety for treatment of a prostate neoplastic condition by linking the therapeutic moiety to a RDC1 binding agent or a binding agent selective for a biomarker polypeptide having a nucleotide or amino acid sequence referenced by GenBank accession number in Table 1. Such targeting is expected to direct a therapeutic moiety selectively to prostate cancer cells, such as androgen-independent cancer cells, and allow sparing of normal cells of the prostate and other organs and tissues.

A variety of therapeutic moieties are known to those skilled in the art. A therapeutic moiety that can be targeted to a prostate cell can be, for example, a cancer chemotherapeutic agent, cytotoxic compound, and gene therapy vector.

An RDC1 binding agent, or a binding agent selective for a biomarker polypeptide having a nucleotide sequence or amino acid sequence referenced by GenBank accession number in Table 1, also can be used to deliver a variety of other moieties to a prostate neoplastic cell. Such other moieties include, for example, a diagnostic moiety and a drug delivery vehicle, which can be a chambered microdevice, a cell, a liposome or a virus, any of which can further contain an agent such as a drug or a nucleic acid. Various moieties and methods for linking a moiety to a molecule are well known in the art and commercially available (see, for example, "Remington's Pharmaceutical Sciences" 18th ed. (Mack Publishing Co. 1990), chapters 89-91; Harlow and Lane, *Antibodies: A laboratory manual* (Cold Spring Harbor Laboratory Press 1988), each of which is incorporated herein by reference.

A compound identified using the screening methods of the invention can be formulated and administered in a manner and in an amount appropriate for the condition to be treated; the weight, gender, age and health of the individual; the biochemical nature, bioactivity, bioavailability and side effects of the particular compound; and in a manner compatible with concurrent treatment regimens. An appropriate amount and formulation for a particular therapeutic application in humans can be extrapolated based on the activity of the compound in in vitro assays for determining compound activity, including cell-based proliferative assays described herein, and from recognized animal models of the particular condition, such as the proliferative condition animal models described herein.

The total amount of a compound administered for testing or therapeutic purposes can be administered as a single dose or by infusion over a relatively short period of time, or can be administered in multiple doses administered over a more prolonged period of time. Additionally, the compound can be administered in a slow-release matrix, which can be implanted for systemic delivery at or near the site of the target tissue. Contemplated matrices useful for controlled release of compounds, including therapeutic compounds, are well known in the art, and include materials such as DepoFoam™, biopolymers, micropumps, and the like.

Compounds can be administered for testing or therapeutic purposes to an animal by routes known in the art including, for example, intravenously, intramuscularly, subcutaneously, intraorbitally, intracapsularly, intraperitoneally, intracisternally, intra-articularly, intracerebrally, orally, intravaginally, rectally, topically, intranasally, or transdermally.

Generally, compounds are administered for testing and therapeutic purposes to an animal as a pharmaceutical composition comprising the compound and a pharmaceutically acceptable carrier. The choice of pharmaceutically acceptable carrier depends on the route of administration of the compound and on its particular physical and chemical characteristics. Pharmaceutically acceptable carriers are well known in the art and include sterile aqueous solvents such as physiologically buffered saline, and other solvents or vehicles such as glycols, glycerol, oils such as olive oil and injectable organic esters. A pharmaceutically acceptable carrier can further contain physiologically acceptable compounds that stabilize the compound, increase its solubility, or increase its absorption. Such physiologically acceptable compounds include carbohydrates such as glucose, sucrose or detrains; antioxidants, such as ascorbic acid or glutathione; chelating agents; and low molecular weight proteins.

For treating a patient, more than one therapeutic approach or compound can be provided to an individual for maximal symptom control. Thus, for use in reducing cell growth a compound identified using the methods of the invention can advantageously be administered concurrently or sequentially with another therapeutic mode or formulated with a second compound that controls the same or related symptoms. For example, in treating a prostate neoplastic condition, a compound identified using the methods of the invention can be administered while an individual is receiving chemotherapy, surgery, such as radical prostatectomy, radiation therapy, cryotherapy and androgen-ablation therapy. The skilled clinician will be able to determine concurrent or sequential therapies appropriate for use with a compound identified using the methods of the invention.

A compound identified using the methods of the invention can be delivered to prostate cells by site-specific means. Cell-type-specific delivery can be provided by conjugating a peptide to a targeting molecule, for example, on that selectively binds to the affected prostate cells. Methods for targeting include conjugates, such as those described in U.S. Pat. No. 5,391,723. Targeting vehicles, such as liposomes, can be used to deliver a compound, for example, by encapsulating the compound in a liposome containing a cell-specific targeting molecule. Methods for targeted delivery of compounds to particular cell types are well-known to those skilled in the art.

It is understood that modifications which do not substantially affect the activity of the various embodiments of this invention are also included within the definition of the invention provided herein. Accordingly, the following examples are intended to illustrate but not limit the present invention.

EXAMPLE I

Identification of Androgen-Regulated Prostate-Specific Genes

This example shows a method for identifying polypeptides having androgen-modulated expression in prostate cancer cells.

Isotope coded affinity tag (ICAT) proteomics technology (see Gygi et al., Nat. Biotechnol. 17:994-999 (1999); WO 00/11208) was used to identify proteins expressed in LNCaP prostate epithelia cells that undergo a change in expression upon treatment with androgen. Multiple proteins resident in the microsomal fraction of LNCaP prostate epithelia cells were found to undergo androgen-regulated expression level changes. Table 1 shows GenBank accession numbers referencing nucleotide and amino acid sequences of proteins having increased or reduced expression in response to androgen.

One of the proteins that had increased expression in response to androgen contained the peptide sequence KTVTSAANNETYCRS (SEQ ID NO:3). This protein was identified to be human RDC1 by sequence database searching, and is referenced as P25106 in the Swiss Prot database.

RNA interference was used to show that a reduction in RDC1 expression in LNCaP cells results in cellular changes, such as increased cell adherence. RNA interference is a process of sequence-specific gene silencing by post-transcriptional RNA degradation, which is initiated by double-stranded RNA (dsRNA) homologous in sequence to the silenced gene.

Figure 1B:
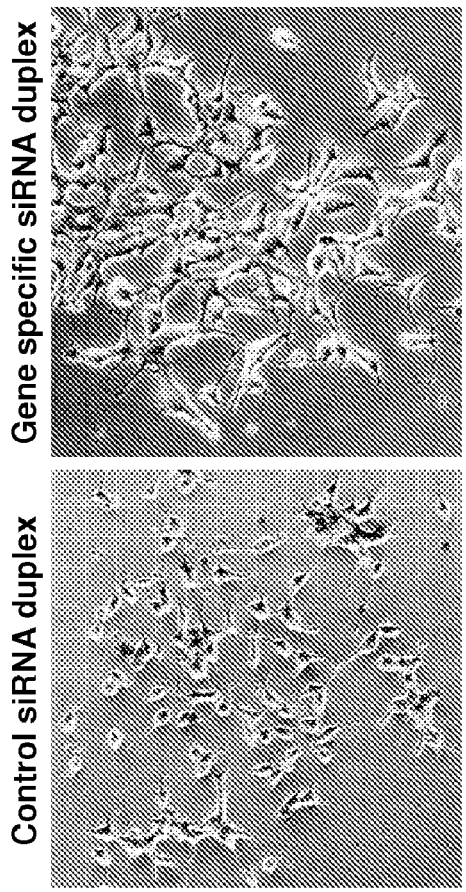

FIG. 1A shows that LNCaP cells starved of androgen have a neuronal-like appearance compared to LNCaP cells growth in androgen-containing medium. FIG. 1A also shows that cells containing an RDC1 gene specific siRNA duplex are more spread out and are attached to the plate more efficiently than cells containing a scrambled siRNA duplex. As shown in FIG. 1B, this effect also was observed in an androgen independent cell line.

Figure 1C:
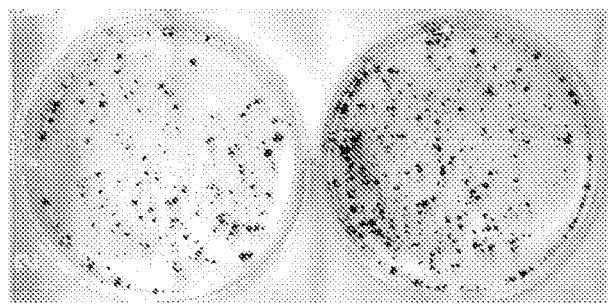

FIG. 1C shows that an increased number of LNCaP cells adhere to the dish after silencing the RDC1 gene. These results show that RDC1 has a role in modulating the phenotype of cells in response to androgen, and that a reduction in RDC1 correlates with a less proliferative phenotype.

Throughout this application various publications have been referenced within parentheses. The disclosures of these publications in their entireties are hereby incorporated by reference in this application in order to more fully describe the state of the art to which this invention pertains.

Although the invention has been described with reference to the disclosed embodiments, those skilled in the art will readily appreciate that the specific experiments detailed are only illustrative of the invention. It should be understood that various modifications can be made without departing from the spirit of the invention.

TABLE 1

Protein and Nucleic Acid Accession Numbers of Prostate Neoplastic Condition Biomarkers

| Gene Name | Ratio | Protein Accession Number | Nucleic Acid Accession Number |
| --- | --- | --- | --- |
| KLK2 | 0.12 | P20151 | M18157 |
| TMPRSS2 | 0.12 | O15393 | U75329 |
| STK39 | 0.13 | | AF099989 |
| F15K9.12 | 0.17 | | AC005278 |
| TTN | 0.18 | | I38346 |
| IKKB | 0.19 | | AF029684 |
| CD9 | 0.20 | P21926 | M38690 |
| FLJ20535 | 0.20 | | AK000542 |
| FDFT1 | 0.22 | P37268 | L06070 |
| KLK3 | 0.25 | P07288 | M27274 |
| PSMB5 | 0.25 | P28074 | D29011 |
| KKIAMRE | 0.26 | | U35146 |
| KPNB3 | 0.26 | O00410 | U72761 |
| NDRG1 | 0.26 | Q92597 | D87953 |
| EPB41 | 0.27 | P11171 | J03796 |
| MICAL | 0.27 | | T34532 |
| PPAP2A | 0.27 | | Y14436 |
| DHCR24 | 0.28 | | AH011158 |
| ELOVL2 | 0.28 | | AL136939 |
| FKBP5 | 0.28 | Q13451 | U71321 |
| HSP75 | 0.28 | Q12931 | AF154108 |
| KIAA1324 | 0.28 | | AB037745 |
| LTF | 0.28 | P02788 | U07643 |
| FACL3 | 0.29 | | D89053 |
| FLJ12465 | 0.30 | | AK022527 |
| RIN1 | 0.31 | Q13671 | L36463 |
| YWHAE | 0.31 | P42655 | U28936 |
| ACADVL | 0.32 | P49748 | D43682 |
| LTBR | 0.32 | P36941 | L04270 |
| AKT3 | 0.33 | Q9Y243 | AF124141 |
| EPS8R2 | 0.33 | | AK025588 |
| KPNA1 | 0.33 | P52294 | BC002374 |
| FASN | 0.34 | P49327 | U26644 |
| IGHV3-7 | 0.34 | | AJ245222 |
| FLJ23251 | 0.35 | | AK026904 |
| RRAS | 0.35 | P10301 | BC016318 |
| ABHD2 | 0.36 | P08910 | X12433 |
| PYGM | 0.36 | P11217 | U94777 |
| SORD | 0.36 | Q00796 | L29008 |
| IGHV | 0.37 | | AJ239387 |
| LSS | 0.37 | P48449 | U22526 |
| AP2A2 | 0.38 | | AB020706 |
| RPS12 | 0.40 | P25398 | AB007153 |

TABLE 1-continued

Protein and Nucleic Acid Accession Numbers of
Prostate Neoplastic Condition Biomarkers

| Gene Name | Ratio | Protein Accession Number | Nucleic Acid Accession Number |
|---|---|---|---|
| unknown | 0.41 | | AC011001 |
| ACACA | 0.41 | Q13085 | U19822 |
| SLC19A2 | 0.41 | O60779 | AF153330 |
| ADAM12 | 0.43 | | S71949 |
| AHCYL1 | 0.43 | O43865 | U82761 |
| KIAA1522 | 0.43 | | AB040955 |
| NAPG | 0.43 | Q99747 | U78107 |
| ACLY | 0.44 | P53396 | U18197 |
| COMT | 0.44 | P21964 | M65212 |
| not named | 0.45 | | U85992 |
| BAIAP2 | 0.45 | | AB015019 |
| SAC3 | 0.45 | Q92562 | D87464 |
| unknown | 0.46 | | T17320 |
| HSPA8 | 0.46 | P11142 | AB034951 |
| LDHA | 0.46 | P00338 | BC000749 |
| ADAMTS1 | 0.47 | Q9UHI8 | AF170084 |
| FLII | 0.47 | | A49674 |
| PRKAA1 | 0.47 | Q13131 | AB022017 |
| PSMD12 | 0.47 | | JC6523 |
| SEC24D | 0.47 | | AB018298 |
| SLC9A3R1 | 0.47 | | AF015926 |
| TUBB4Q | 0.47 | | U83668 |
| B2M | 0.48 | P01884 | M17987 |
| CRIP2 | 0.48 | P52943 | D42123 |
| KIAA0603 | 0.48 | | T00261 |
| PYGB | 0.48 | P11216 | J03544 |
| VDU1 | 0.48 | | AB029020 |
| ACTN4 | 0.50 | | U48734 |
| LIM | 0.50 | | AF061258 |
| PYCR1 | 0.50 | P32322 | M77836 |
| RAB3B | 0.50 | P20337 | M28214 |
| ADTG | 0.51 | O43747 | AB015317 |
| ANXA4 | 0.51 | P09525 | M19383 |
| DNAJC3 | 0.51 | | JC4775 |
| GYG | 0.51 | P46976 | U44131 |
| PRPSAP2 | 0.51 | | AB007851 |
| TARS | 0.51 | P26639 | M63180 |
| SLC1A5 | 0.52 | Q15758 | U53347 |
| ESD | 0.53 | P10768 | AF112219 |
| GLUL | 0.53 | P15104 | BC010037 |
| MYO1C | 0.53 | | A59253 |
| UBE2N | 0.53 | Q16781 | D83004 |
| VCL | 0.53 | P18206 | M33308 |
| KIAA1607 | 0.54 | | AF060225 |
| MYO1B | 0.54 | | AK022489 |
| CFL1 | 0.55 | P23528 | BC012265 |
| LDLR | 0.55 | P01130 | BC014514 |
| COPS4 | 0.56 | | AF100757 |
| DDX36 | 0.56 | | AF217190 |
| DSTN | 0.56 | P18282 | BC009477 |
| LCP1 | 0.56 | P13796 | M22300 |
| MYH6 | 0.56 | P13533 | D00943 |
| NAPA | 0.56 | P54920 | U39412 |
| RAB4A | 0.56 | P20338 | M28211 |
| ATP1B3 | 0.57 | P54709 | U51478 |
| FLJ10209 | 0.57 | | AB033001 |
| KIAA1102 | 0.57 | | AB029025 |
| TDE1 | 0.57 | | AF112227 |
| ABCC1 | 0.58 | P33527 | L05628 |
| ACTR3 | 0.58 | P32391 | AF006083 |
| AGR2 | 0.58 | | JE0350 |
| ARMET | 0.58 | P55145 | M83751 |
| CD2AP | 0.58 | | T13151 |
| FLJ20986 | 0.58 | | AK024639 |
| MYO5A | 0.58 | | A53016 |
| NSDHL | 0.58 | Q15738 | U47105 |
| HSPA4 | 0.59 | P34932 | AB023420 |
| KIAA0601 | 0.59 | | AB011173 |
| MSN | 0.59 | P26038 | M69066 |
| RAP1B | 0.59 | P09526 | BC000176 |
| STK24 | 0.59 | | AF024636 |
| CAP | 0.60 | Q01518 | M98474 |
| DIA1 | 0.60 | P00387 | BC004821 |
| FKBP2 | 0.60 | | JC1365 |
| PSMA5 | 0.60 | P28066 | X61970 |
| AOP2 | 0.61 | P30041 | D14662 |
| BAP29 | 0.61 | | AC004839 |
| MAGED2 | 0.61 | Q9UNF1 | AF128527 |
| MRP4 | 0.61 | O15439 | AY081219 |
| AblBP4 | 0.62 | | AF001628 |
| CSRP1 | 0.62 | P21291 | M33146 |
| EGFR | 0.62 | P00533 | U48722 |
| HBXIP | 0.62 | O43504 | AF029890 |
| HSPA1A | 0.62 | P08107 | M59828 |
| PTD004 | 0.62 | | T46901 |
| sialic acid-specific acetylesterase II | 1.60 | | T46250 |
| HSPA5 | 1.60 | | AF188611 |
| XPO1 | 1.60 | | D89729 |
| PXF | 1.61 | P40855 | AB018541 |
| RPA3 | 1.61 | P35244 | L07493 |
| ALDH3A2 | 1.62 | P51648 | L47162 |
| BAT1 | 1.62 | Q13838 | BC000361 |
| CS | 1.62 | O75390 | AF047042 |
| CTSB | 1.62 | P07858 | M14221 |
| RPL12 | 1.62 | P30050 | L06505 |
| RPL14 | 1.63 | P50914 | U16738 |
| RPL17 | 1.63 | P18621 | BC000502 |
| CUL2 | 1.64 | Q13617 | U83410 |
| HNRPA0 | 1.64 | Q13151 | U23803 |
| MCM4 | 1.65 | P33991 | U63630 |
| MTHFD1 | 1.65 | P11586 | J04031 |
| ARHGAP5 | 1.66 | | U17032 |
| HNRPH1 | 1.66 | P31943 | L22009 |
| MRPL15 | 1.66 | | AF161494 |
| PTK7 | 1.66 | Q13308 | U33635 |
| DDX1 | 1.67 | Q92499 | X70649 |
| FTH1 | 1.67 | P02794 | M11146 |
| HADH2 | 1.67 | Q99714 | U96132 |
| KIAA0090 | 1.67 | | AL035413 |
| C14orf3 | 1.68 | | AF111168 |
| MAOA | 1.68 | P21397 | M68840 |
| HSPD1 | 1.69 | P10809 | M22382 |
| LOC221927 | 1.69 | | T42692 |
| RPL37A | 1.69 | P12751 | L06499 |
| C9orf10 | 1.70 | | AF214737 |
| EIF2S2 | 1.70 | P20042 | M29536 |
| GDI2 | 1.70 | P50395 | D13988 |
| FLJ20859 | 1.71 | | AK024512 |
| HNRPDL | 1.72 | | JW0079 |
| ATP2B1 | 1.73 | P20020 | J04027 |
| BUB3 | 1.73 | O43684 | AF047472 |
| CAPN1 | 1.73 | P07384 | BC008751 |
| KTN1 | 1.73 | | I53799 |
| PCBP2 | 1.73 | Q15366 | X78136 |
| HSD17B4 | 1.74 | P51659 | AF057740 |
| PRKDC | 1.74 | | A57099 |
| RENT1 | 1.74 | | AC003972 |
| BDH | 1.76 | Q02338 | M93107 |
| LOC55829 | 1.76 | | AF157317 |
| MRPL22 | 1.76 | | AF161507 |
| SNRPF | 1.76 | Q15356 | BC002505 |
| ZNF345 | 1.79 | Q14585 | X78933 |
| ALEX3 | 1.80 | | AB039669 |
| GLA | 1.80 | P06280 | U78027 |
| H2AFY | 1.80 | | AF041483 |
| RBBP4 | 1.80 | Q09028 | BC003092 |
| RPL44 | 1.80 | P09896 | M15661 |
| LOC51292 | 1.81 | | AB032903 |
| DDX9 | 1.82 | Q08211 | L13848 |
| FDXR | 1.82 | P22570 | J03826 |
| SDF2L1 | 1.84 | | AB043007 |
| SLC25A4 | 1.84 | P12235 | J02966 |
| ANK3 | 1.85 | | A55575 |
| ASNS | 1.85 | P08243 | L35946 |
| JAM1 | 1.85 | Q9Y624 | AF111713 |
| HADHB | 1.87 | P55084 | D16481 |
| NDUFS1 | 1.87 | P28331 | X61100 |

TABLE 1-continued

Protein and Nucleic Acid Accession Numbers of
Prostate Neoplastic Condition Biomarkers

| Gene Name | Ratio | Protein Accession Number | Nucleic Acid Accession Number |
|---|---|---|---|
| ZNF9 | 1.87 | P20694 | M28372 |
| FLJ10581 | 1.89 | | AF177344 |
| SFRS2IP | 1.89 | | T09073 |
| DPP7 | 1.90 | | AF154502 |
| RNPC2 | 1.92 | | I55595 |
| FBRNP | 1.93 | P51991 | S63912 |
| P17.3 | 1.93 | | AK000501 |
| ANK1 | 1.94 | P16157 | M28880 |
| GAA | 1.94 | P10253 | M34424 |
| ITGB1 | 1.94 | P05556 | AH003217 |
| RNASE6 | 1.94 | | S78046 |
| COPA | 1.95 | P53621 | U24105 |
| GLG1 | 1.95 | | U64791 |
| ME2 | 1.96 | P23368 | M55905 |
| PRDX3 | 1.96 | P30048 | D49396 |
| TACSTD1 | 1.96 | P16422 | M32325 |
| CFR-1 | 1.97 | | U28811 |
| HADHA | 1.97 | P40939 | D16480 |
| MTCO1 | 1.97 | P00395 | D38112 |
| PLXNB1 | 1.97 | | AB007867 |
| ZNF147 | 1.97 | | A49656 |
| HINT3 | 1.98 | | AL035689 |
| SHMT2 | 1.98 | P34897 | U23143 |
| ETFB | 1.99 | P38117 | X71129 |
| KIAA1583 | 1.99 | | AB046803 |
| SERPINB6 | 1.99 | | S69272 |
| VDAC2 | 1.99 | P45880 | L08666 |
| CTSH | 2.00 | P09668 | BC002479 |
| PLCB4 | 2.00 | | AL023805 |
| UBA52 | 2.00 | P14793 | U25064 |
| DNASE2 | 2.01 | O00115 | AB004574 |
| C(27)-3BETA-HSD | 2.02 | | AF277719 |
| RPL24 | 2.02 | P38663 | M94314 |
| SLC25A3 | 2.02 | | B53737 |
| SNRPD2 | 2.02 | P43330 | U15008 |
| hypo unknown | 2.03 | | AF242773 |
| PHF5A | 2.03 | Q9UH06 | BC007321 |
| SGSH | 2.03 | P51688 | U30894 |
| ZFP67 | 2.03 | | AF007833 |
| FLJ22169 | 2.04 | | AK025822 |
| IDH2 | 2.04 | P48735 | BC009244 |
| PLRG1 | 2.05 | | AF043250 |
| U2AF65 | 2.05 | P26368 | X64044 |
| DDX6 | 2.06 | P26196 | D17532 |
| CTL1 | 2.08 | | AJ245620 |
| CYC1 | 2.10 | P08574 | J04444 |
| NDUFA8 | 2.10 | P51970 | AF044953 |
| CSNK2B | 2.11 | P13862 | M30448 |
| SNRP70 | 2.11 | P08621 | M22636 |
| U5-116KD | 2.11 | | D21163 |
| NDRG2 | 2.12 | Q9UN36 | AF30405 |
| NTF2 | 2.12 | P13662 | BC002348 |
| CSRP3 | 2.13 | P49006 | BC007904 |
| FLJ12528 | 2.13 | | AK022590 |
| MAN2B1 | 2.14 | O00754 | U60266 |
| ATP5C1 | 2.15 | P36542 | D16561 |
| KIAA0042 | 2.15 | | D26361 |
| SLC25A13 | 2.16 | | AC002540 |
| HNRPD | 2.17 | | A54601 |
| MSH3 | 2.18 | P20585 | J04810 |
| NDUFV1 | 2.18 | P49821 | AF053069 |
| RPS16 | 2.18 | P17008 | M60854 |
| BRF1 | 2.19 | Q07352 | BC018340 |
| NRP1 | 2.20 | O14786 | AF018956 |
| NHP2L1 | 2.21 | P55769 | D50420 |
| MDS029 | 2.22 | | AF220049 |
| TIMM8A | 2.22 | | AF150087 |
| C1QBP | 2.23 | Q07021 | L04636 |
| CAT | 2.24 | P04040 | AL035079 |
| MRPS30 | 2.24 | | AF146192 |
| PPIF | 2.24 | P30405 | M80254 |
| SDHB | 2.24 | P21912 | U17248 |
| UQCRC1 | 2.24 | P31930 | L16842 |
| WWP2 | 2.25 | | U96114 |
| GALNAC-T3 | 2.26 | | X92689 |
| DDX5 | 2.27 | P17844 | AF015812 |
| NDUFB7 | 2.27 | P17568 | M33374 |
| C21orf33 | 2.28 | P30042 | D86061 |
| ZNF142 | 2.28 | P52746 | D87073 |
| MDH2 | 2.29 | P40926 | AF047470 |
| RPA1 | 2.30 | P27694 | M63488 |
| LOC51631 | 2.31 | | AF151817 |
| MGST3 | 2.31 | O14880 | AF026977 |
| FLJ10852 | 2.32 | | AK001714 |
| MIF | 2.34 | P14174 | BC022414 |
| U2AF35 | 2.34 | Q01081 | M96982 |
| ETFA | 2.36 | P13804 | J04058 |
| SQRDL | 2.36 | | AF042284 |
| UQCRH | 2.36 | P07919 | M36647 |
| VDAC1 | 2.36 | P21796 | L06132 |
| MATR3 | 2.37 | | AB018266 |
| MAZ | 2.37 | P56270 | M94046 |
| ATP5A1 | 2.38 | P25705 | D14710 |
| TFPI | 2.40 | P10646 | J03225 |
| CGI-51 | 2.42 | | AF151809 |
| RPS20 | 2.42 | P17075 | L06498 |
| UQCRC2 | 2.42 | P22695 | J04973 |
| IGFBP2 | 2.43 | P18065 | M35410 |
| ACAT1 | 2.44 | P24752 | D10511 |
| PCK2 | 2.45 | Q16822 | BC001454 |
| TOP1 | 2.45 | P11387 | J03250 |
| UQCRFS1 | 2.45 | P47985 | AAC41754 |
| RPS2 | 2.46 | P15880 | BC001795 |
| HNRPA1 | 2.48 | P09651 | X12671 |
| HNRPU | 2.48 | Q00839 | AF068846 |
| SDHA | 2.48 | P31040 | D30648 |
| VDAC3 | 2.48 | Q9Y277 | AF038962 |
| HPCL2 | 2.53 | | AF161397 |
| SLC25A5 | 2.53 | P05141 | M57424 |
| GRB10 | 2.55 | Q13322 | U34355 |
| SLC25A6 | 2.57 | P12236 | BC007295 |
| DDX17 | 2.58 | Q92841 | U59321 |
| MTCH2 | 2.58 | | AF085361 |
| ATP2C1 | 2.59 | P98194 | AF181120 |
| NIPSNAP1 | 2.60 | | AJ001258 |
| CLN2 | 2.62 | O14773 | AF017456 |
| PURA | 2.62 | Q00577 | M96684 |
| WDR18 | 2.62 | | AC004528 |
| SF3B3 | 2.63 | Q15393 | D87686 |
| ADD1 | 2.64 | P35611 | S70314 |
| LOC222217 | 2.64 | | AC004957 |
| PNUTL1 | 2.64 | Q99719 | U74628 |
| ATP5H | 2.67 | O75947 | AF087135 |
| NDUFS5 | 2.69 | O43920 | AF047434 |
| PCDHA4 | 2.70 | | AC005609 |
| LOC89941 | 2.73 | | AK024450 |
| PRSS8 | 2.73 | Q16651 | L41351 |
| FXR1 | 2.74 | P51114 | U25165 |
| COX6B | 2.77 | P14854 | BC001015 |
| DECR1 | 2.78 | | AL023881 |
| SRI | 2.86 | P30626 | L12387 |
| LU | 2.88 | P50895 | X83425 |
| SELENBP1 | 2.89 | Q13228 | U29091 |
| EIF4E | 2.94 | P06730 | M15353 |
| VRK1 | 2.94 | | AB000449 |
| LMNA | 2.95 | P02545 | X03444 |
| PFKP | 2.96 | Q01813 | D25328 |
| SIAT4A | 2.99 | Q11201 | L29555 |
| H3F3A | 3.08 | P06351 | M11354 |
| SCRIB | 3.09 | D63481 | BAA09768 |
| IL1RAP | 3.20 | | AB006537 |
| LMNB1 | 3.22 | P20700 | M34458 |
| SRP14 | 3.24 | P37108 | X73459 |
| CDYL | 3.26 | | T08789 |
| DEGS | 3.29 | | AF002668 |
| GPD2 | 3.30 | P43304 | U12424 |
| NONO | 3.38 | Q15233 | L14599 |
| FLJ12525 | 3.46 | | AK022587 |

TABLE 1-continued

Protein and Nucleic Acid Accession Numbers of
Prostate Neoplastic Condition Biomarkers

| Gene Name | Ratio | Protein Accession Number | Nucleic Acid Accession Number |
|---|---|---|---|
| SLC4A2 | 3.57 | P04920 | X62137 |
| LAMC1 | 3.60 | P11047 | M55210 |
| SFRS7 | 3.66 | Q16629 | L22253 |
| RDC1 | 3.86 | P25106 | M64749 |
| PLA2G2A | 3.94 | P14555 | M22430 |
| ST14 | 3.98 | | AF057145 |
| GALNT7 | 4.00 | | AJ002744 |
| ATP9A | 5.29 | O75110 | AB014511 |
| VL1 | 7.61 | | AJ278775 |

TABLE 1-continued

Protein and Nucleic Acid Accession Numbers of
Prostate Neoplastic Condition Biomarkers

| Gene Name | Ratio | Protein Accession Number | Nucleic Acid Accession Number |
|---|---|---|---|
| hypothetical unknown | 7.89 | | S12444 |
| USP24 | 9.55 | | AB028980 |
| DGKG | 10.54 | P49619 | D26135 |

Ratio refers to the d0:d8 ratio obtained using ICAT technology where d0 corresponds to "minus androgen" and d8 corresponds to "plus androgen."

What is claimed is:

1. A method to determine whether a sample containing prostate cells is stimulated to proliferate in response to androgen, which method comprises:
   (a) contacting a first portion of said sample with androgen;
   (b) measuring the level of RDC1 expression in said first portion;
   (c) measuring the expression level of RDC1 in a second portion of said sample wherein said second portion has not been treated with androgen;
   (d) comparing the expression level in (b) to the expression level in (c); and
   (e) determining that the cells in said sample are stimulated to proliferate in response to androgen if the level of expression in (b) is higher than the level of expression in (c).

2. The method of claim 1, wherein said prostate cells are neoplastic prostate cells.

3. The method of claim 1, wherein said level of RDC1 is RDC1 polypeptide level.

4. The method of claim 3, wherein said RDC1 polypeptide comprises amino acid sequence SEQ ID NO:2.

5. The method of claim 3, wherein said level of RDC1 polypeptide is measured using an RDC1 binding agent.

6. The method of claim 5, wherein said binding agent is an antibody.

7. The method of claim 1, wherein said sample is obtained from a subject with metastatic prostate cancer.

* * * * *